(12) United States Patent
Nobis et al.

(10) Patent No.: US 12,128,243 B2
(45) Date of Patent: Oct. 29, 2024

(54) DEVICES FOR SUPPLYING ENERGY TO AN ACTIVE EYE IMPLANT

(71) Applicant: Carl Zeiss AG, Oberkochen (DE)

(72) Inventors: Thomas Nobis, Leipzig (DE); Tobias Schmitt-Manderbach, Kempten (DE); Matthias Hillenbrand, Jena (DE)

(73) Assignee: Carl Zeiss AG, Oberkochen (DE)

( * ) Notice: Subject to any disclaimer, the term of this patent is extended or adjusted under 35 U.S.C. 154(b) by 513 days.

(21) Appl. No.: 17/601,062

(22) PCT Filed: Apr. 2, 2020

(86) PCT No.: PCT/EP2020/059407
§ 371 (c)(1),
(2) Date: Oct. 2, 2021

(87) PCT Pub. No.: WO2020/201426
PCT Pub. Date: Oct. 8, 2020

(65) Prior Publication Data
US 2022/0203105 A1  Jun. 30, 2022

(30) Foreign Application Priority Data
Apr. 3, 2019  (DE) .......................... 102019108679.5

(51) Int. Cl.
*A61N 1/378*  (2006.01)
*A61N 1/05*  (2006.01)
(Continued)

(52) U.S. Cl.
CPC ......... *A61N 1/3787* (2013.01); *A61N 1/0543* (2013.01); *G02B 5/32* (2013.01);
(Continued)

(58) Field of Classification Search
None
See application file for complete search history.

(56) References Cited

U.S. PATENT DOCUMENTS 6,915,062 B2  7/2005  Hulse et al.
7,008,099 B2  3/2006  Yamashita et al.
(Continued)

FOREIGN PATENT DOCUMENTS

CN  105281003 A  1/2016
DE  10315397 A1  10/2004
(Continued)

OTHER PUBLICATIONS

Office Action to a parallel European Patent Application rendered by the European Patent Office (EPO) on Jun. 12, 2023, 10 pages (including English translation).
(Continued)

*Primary Examiner* — Darryl J Collins
(74) *Attorney, Agent, or Firm* — Skaar Ulbrich Macari, P.A.

(57) ABSTRACT

A device for supplying power to an active ocular implant in an eye of a user can include a spectacle lens with a first main surface and a second main surface, a light source, and an optical arrangement which is configured to input couple light from the light source into the spectacle lens and output couple said light from the first main surface of the spectacle lens to the user. The optical arrangement can include at least one diffractive element which is arranged in the spectacle lens. Each of the at least one diffractive element can have an associated first end and an associated second end. The associated first end and the associated second end each can have a different distance from the first main surface and/or each have a different distance from the second main surface.

20 Claims, 19 Drawing Sheets

(51) Int. Cl.
  *G02B 5/32* (2006.01)
  *G02B 27/09* (2006.01)
  *G02C 11/00* (2006.01)
  *G03H 1/02* (2006.01)
  *G03H 1/28* (2006.01)
  *H02J 50/30* (2016.01)

(52) U.S. Cl.
  CPC .......... *G02B 27/0944* (2013.01); *G02C 11/10* (2013.01); *G03H 1/0248* (2013.01); *G03H 1/28* (2013.01); *H02J 50/30* (2016.02)

(56) References Cited

U.S. PATENT DOCUMENTS

| | | |
|---|---|---|
| 7,729,572 B1 | 6/2010 | Pepper et al. |
| 8,320,032 B2 | 11/2012 | Levola |
| 8,377,120 B2 | 2/2013 | Lipshitz et al. |
| 9,084,564 B2 | 7/2015 | Bublitz et al. |
| 9,474,902 B2 | 10/2016 | Gefen et al. |
| 10,831,031 B2 | 11/2020 | Rudolph et al. |
| 10,983,338 B2 | 4/2021 | Hegyi |
| 11,137,531 B2 | 10/2021 | Singer et al. |
| 11,624,918 B2 | 4/2023 | Dobschal |
| 2002/0149924 A1 | 10/2002 | Falicoff et al. |
| 2002/0186919 A1 | 12/2002 | Pepper |
| 2005/0286266 A1 | 12/2005 | Park |
| 2006/0028726 A1 | 2/2006 | Ushigome |
| 2006/0126179 A1 | 6/2006 | Levola |
| 2010/0231693 A1 | 9/2010 | Levola |
| 2012/0013962 A1 | 1/2012 | Subbaraman et al. |
| 2014/0140091 A1 | 5/2014 | Vasylyev |
| 2014/0232651 A1 | 8/2014 | Kress et al. |
| 2014/0376207 A1 | 12/2014 | Futterer |
| 2015/0049509 A1 | 2/2015 | Meyers et al. |
| 2015/0182748 A1 | 7/2015 | Gefen et al. |
| 2016/0070113 A1 | 3/2016 | Travis |
| 2016/0231567 A1 | 8/2016 | Saarikko et al. |
| 2016/0231568 A1 | 8/2016 | Saarikko et al. |
| 2017/0160548 A1 | 6/2017 | Woltman et al. |
| 2017/0205618 A1 | 7/2017 | Basset et al. |
| 2018/0067318 A1 | 3/2018 | St. Hilaire |
| 2018/0232048 A1 | 8/2018 | Popovich et al. |
| 2018/0364409 A1 | 12/2018 | Lee et al. |
| 2019/0046798 A1 | 2/2019 | Kindt et al. |
| 2019/0187465 A1 | 6/2019 | Erler et al. |
| 2019/0204594 A1 | 7/2019 | Hegyi |
| 2019/0391377 A1 | 12/2019 | Stoppe et al. |
| 2020/0103675 A1 | 4/2020 | Schwarz et al. |
| 2022/0019091 A1 | 1/2022 | Nobis et al. |
| 2022/0203106 A1 | 6/2022 | Nobis et al. |
| 2022/0206208 A1 | 6/2022 | Hillenbrand et al. |

FOREIGN PATENT DOCUMENTS

| | | |
|---|---|---|
| DE | 102017130344 A1 | 6/2019 |
| GB | 2411248 A | 8/2005 |
| JP | 2017156389 A | 9/2017 |
| KR | 20150065137 A | 6/2015 |
| WO | 2015101932 A2 | 7/2015 |
| WO | 2015151255 A1 | 10/2015 |
| WO | 2015167492 A1 | 11/2015 |
| WO | 2016149416 A1 | 9/2016 |
| WO | 2017180403 A1 | 10/2017 |
| WO | 2018204712 A1 | 11/2018 |

OTHER PUBLICATIONS

Office Action to a parallel U.S. Appl. No. 17/600,857 rendered by the United States Patent and Trademark Office on Jul. 6, 2023, 16 pages.
Office Action to a parallel Japanese Patent Application rendered by the Japan Patent office on Sep. 5, 2023, 18 pages (including summary English translation).
International Search Report (and its English-language translation) from parallel International Patent Application No. PCT/EP20/59118, dated Jul. 20, 2020, 9 pages.
Written Opinion (and its English-language translation) from parallel International Patent Application No. PCT/EP20/59118, dated Jul. 20, 2020, 11 pages.
International Search Report (and its English-language translation) from parallel International Patent Application No. PCT/EP20/59409, dated Jun. 29, 2020, 5 pages.
Written Opinion (and its English-language translation) from parallel International Patent Application No. PCT/EP20/59409, dated Jun. 29, 2020, 9 pages.
Search Report (and its English-language translation) from German Application No. DE 10 2019 108 679.5, dated Dec. 12, 2019, 10 pages.
Search Report (and its English-language translation) from German Application No. DE 10 2019 108 678.7, dated Dec. 11, 2019, 11 pages.
Office Action to a parallel U.S. Appl. No. 17/600,857 rendered by the United States Patent and Trademark Office on Jan. 9, 2024, 14 pages.
International Search Report rendered by the International Bureau of WIPO for PCT/EP2020/059407, dated Jun. 24, 2020, 2 pages.
Written Opinion rendered by the International Bureau of WIPO for PCT/EP2020/059407, dated Jun. 24, 2020, 5 pages.
Office Action to the corresponding German Patent Application rendered on Feb. 29, 2020, 14 pages (including partial English translation).
Office Action to a parallel U.S. Appl. No. 17/600,857 rendered by the United States Patent and Trademark Office on Mar. 21, 2024, 16 pages.
Office Action to a parallel Japanese Patent Application rendered by the Japan Patent Office on Feb. 20, 2024, 17 pages (including summary English translation).

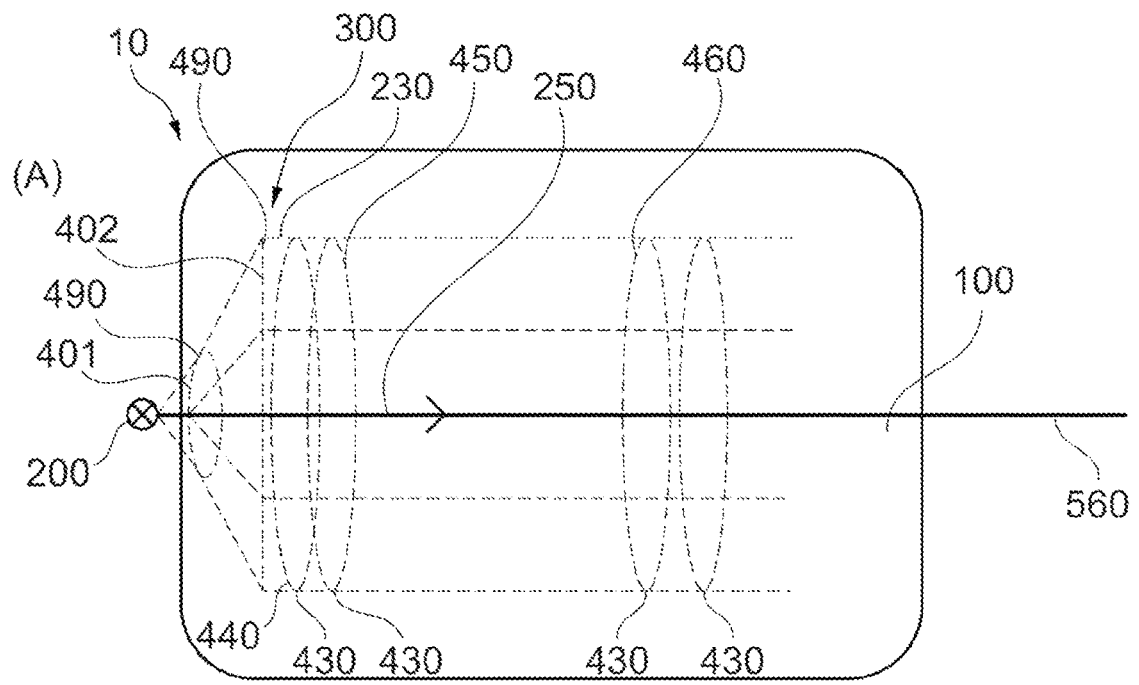
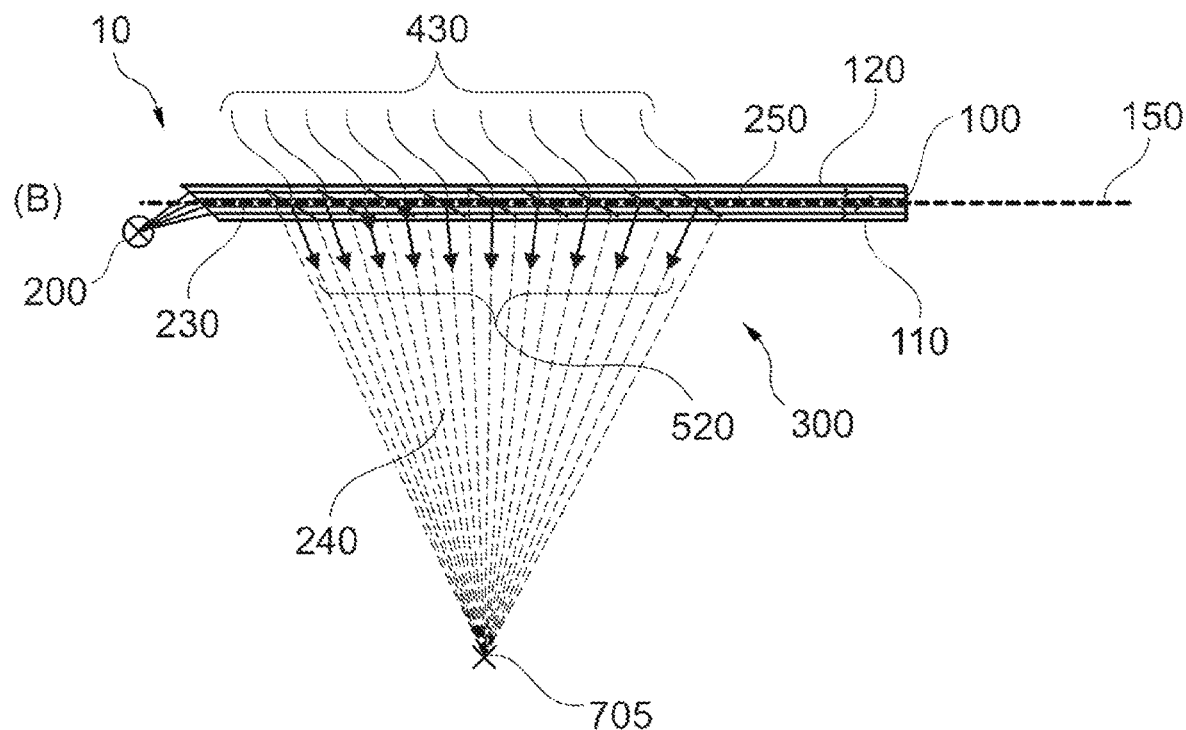
Fig. 12

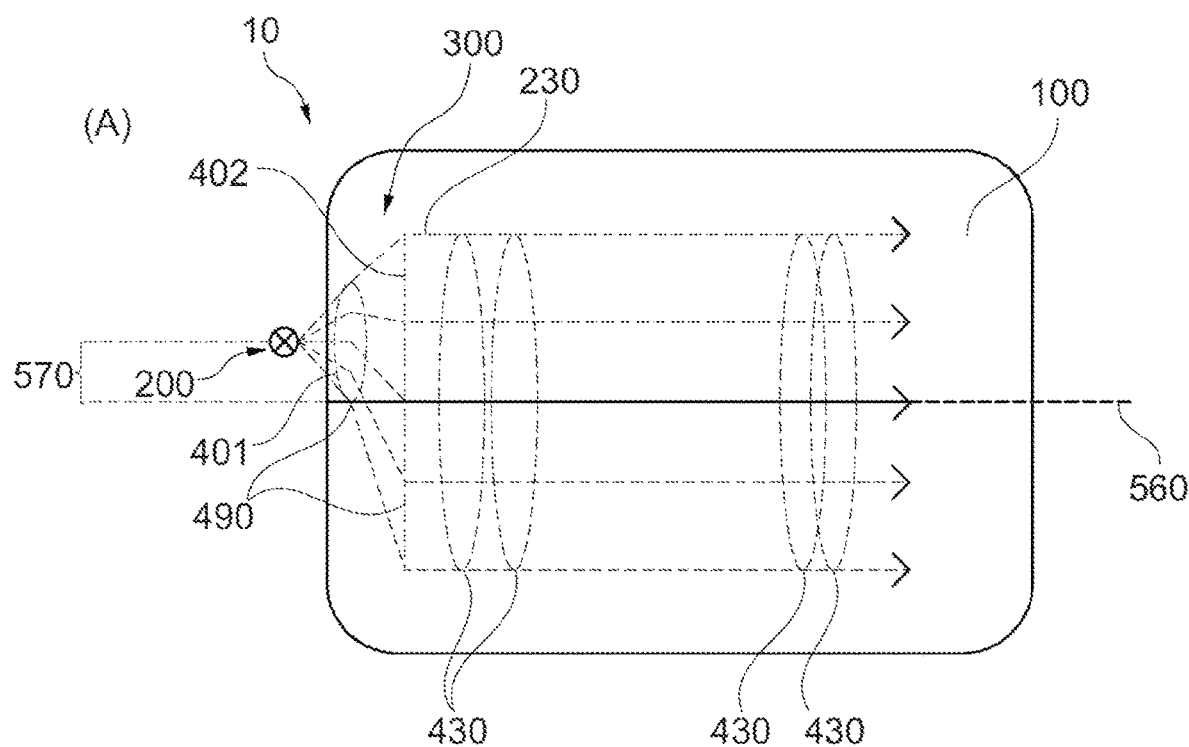
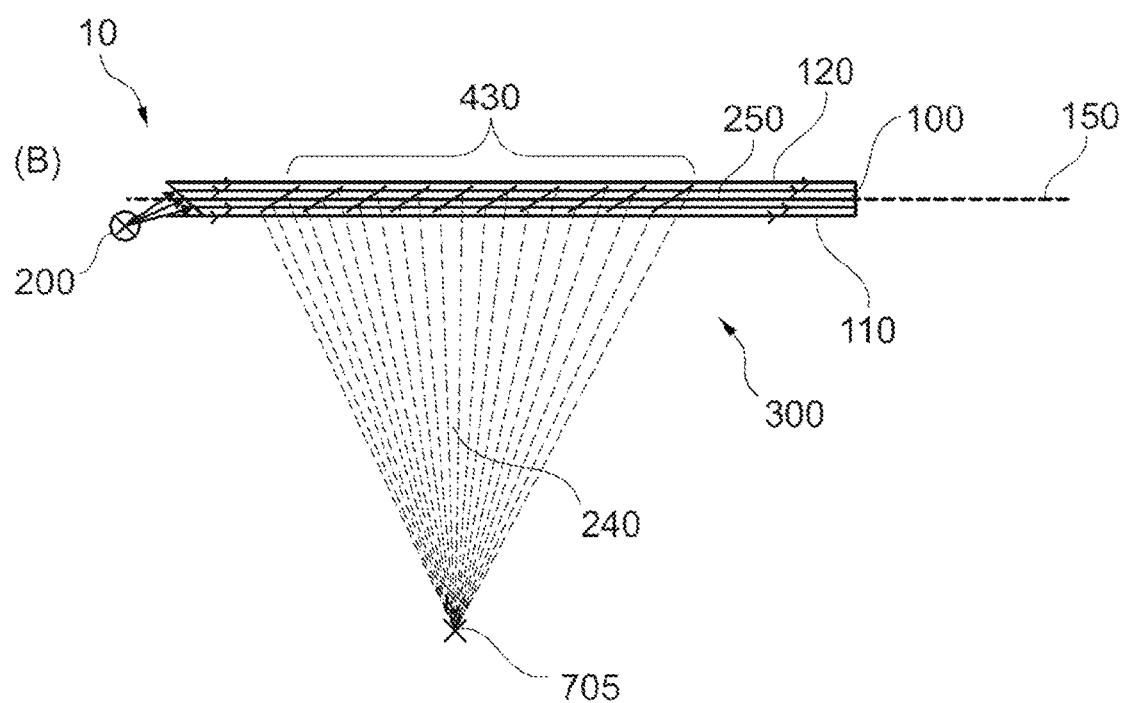
Fig. 14

DEVICES FOR SUPPLYING ENERGY TO AN ACTIVE EYE IMPLANT

PRIORITY

This application claims the priority of German patent application DE 10 2019 108 679.5, filed Apr. 3, 2019, which is hereby incorporated herein by reference in its entirety.

FIELD

The present application relates to devices for supplying power to an active ocular implant by means of light.

BACKGROUND

In this case, active ocular implants are devices which are implanted into an eye of a patient in order to carry out certain functions there. Retinal implants are examples of such active ocular implants. Retinal implants have been developed to restore vision, at least to a certain degree, for persons who have lost the ability to see but who still have a connection from the optic nerve to the brain. Such retinal implants usually comprise an image sensor which produces—optionally with additional circuits—electric pulses that are then registered via the optic nerve.

Other examples of active ocular implants are actively accommodating intraocular lenses or implanted sensors for measuring parameters in the eye, for example the blood sugar level in the aqueous humor. In contrast to passive implants (e.g., simple lenses), such active ocular implants require electric energy in order to be operated.

One option for the energy supply lies in the supply of light, for example infrared radiation, below the visible range of the spectrum of light, which is then converted into electric energy by the active ocular implant, essentially by means of a solar cell or a similar device. However, a supply with other light wavelengths is possible as a matter of principle.

An interface between this external optical system and the human eye with the relevant implant must meet a number of requirements. By way of example, these are based on anatomical features of the human eye, on the usual viewing habits in the considered case or on demands relating to the harmlessness of the utilized radiation to health.

The power transferred by the radiation can also serve for communication with the active ocular implant, for example by modulating the intensity and/or frequency of the transferred radiation.

Devices for supplying the ocular implant can be provided as spectacle lenses for example, optionally with further components outside of the pair of spectacles.

DE 10 2017 107 346 A1 has disclosed such an device with volume holograms for supplying active ocular implants. In such conventional devices, the aperture angle of the light cone emanating from the device scales with the thickness of the spectacle lens, wherein a full aperture angle of approximately 40° can be realized in the case of a thickness of approximately 5 mm.

Further, the volume holograms in DE 2017 107 346 A1 are illuminated by a collimated light beam that extends through the spectacle lens. Therefore, it is necessary to provide the illumination light over the full height of the output coupling holograms, which makes the structure comparatively complicated and may lead to a relatively large amount of space required for the installation.

SUMMARY

It is an object of certain embodiments to provide devices for supplying power to active ocular implants with large illumination angles even in the case of a thin spectacle lens, to allow more flexible arrangements in relation to the illumination light and to avoid shadowed regions.

To supply power to active ocular implants it is desirable if the power supply is ensured independently of the line of sight of the user. This may have a high power consumption as a consequence in conventional devices since the illumination needs to be set up such that sufficient light is available for the active ocular implant for each viewing angle and each pupil dimension. The illumination region is under active control in other devices, for example by means of "eye tracking". However, this conventionally needs complex arrangements that have a significant volume.

An object of certain embodiments is to improve the energy efficiency of such devices and offer improved options for a selective illumination of active ocular implants from different directions.

The disclosure includes a device for supplying power to an active ocular implant in an eye of a user.

In certain embodiments, the device comprises a spectacle lens with a first main surface and a second main surface, and comprises a light source and an optical arrangement. The optical arrangement is configured to input couple light from the light source into the spectacle lens and output couple said light from the first main surface of the spectacle lens to the user.

In this case, the optical arrangement comprises at least one diffractive element arranged in the spectacle lens. Each diffractive element of the at least one diffractive element has an associated first end and an associated second end, wherein the associated first end and the associated second end each have a different distance from the first main surface and/or each have a different distance from the second main surface. Expressed differently, the at least one diffractive element is arranged at an angle in the spectacle lens.

Thus, the at least one diffractive element can be arranged at an angle to the first main surface and/or the second main surface. The angle can be greater than 1° and/or greater than 5° and/or greater than 10° and/or greater than 30° and/or greater than 50° and/or greater than 70° and/or greater than 80° and/or greater than 85°.

The optical arrangement can comprise one or more further optical elements, for example one or more further diffractive elements. The further optical element or elements can have a different arrangement to the at least one diffractive element. By way of example, one or more of the optical elements can be arranged parallel or perpendicular to the first and/or the second main surface.

The first main surface and the second main surface can each be arranged such that a user of the spectacle lens gazes through the first main surface and the second main surface in the case of the zero line of sight when wearing spectacles with the spectacle lens.

The light source can emit light substantially outside of the range visible to humans, for example it can be an infrared light source. This can be a light-emitting diode, laser radiation or any other type of light source.

The at least one diffractive element can be any combination of different diffractive elements. By way of example, these can be conventional diffractive elements such as kinoforms or surface gratings.

In this case, a kinoform is understood to mean a diffractive element with a periodic height profile. By way of example, the periodic height profile can be a sawtooth profile.

The diffractive element can be a volume hologram.

The at least one diffractive element being arranged in the spectacle lens is understood to mean that it is at least partly, in particular completely, surrounded by the material of the spectacle lens. This type of arrangement is sometimes also referred to as "buried".

In some cases where the at least one diffractive element is a volume hologram, the volume hologram could have been generated by means of laser writing in the spectacle lens, for example.

Such volume holograms per se are known from for example DE 10 2016 115 938 A1, but other volume holograms can also be implemented.

In cases where the at least one diffractive element is made up by conventional diffractive elements, the spectacle lens can be manufactured from at least two different materials with different refractive indices, wherein the at least one diffractive element can be arranged such that it is arranged at the interface between the at least two materials.

The device can be held by a spectacle frame. It can be embodied so as to be able to be worn on the head of a user, for example as a pair of spectacles.

The at least one diffractive element can comprise a first diffractive element. The latter can be configured to receive a collimated light beam and provide the latter as a divergent light beam.

This is advantageous in that a smaller region in the spectacle lens is required than has previously been the case for the purposes of input coupling the light, but light can nevertheless be output coupled by way of the first main surface to the user over a greater surface than would be the case without the obliquely arranged first diffractive element.

The at least one diffractive element can comprise a second diffractive element. The latter can be configured to receive the divergent light beam from the first diffractive element and provide said divergent light beam as an expanded light beam.

The expanded light beam can extend substantially parallel to the first main surface and/or second main surface. In the cases where the main surfaces are not planes, for example because the spectacle lens relates to convex or concave forms, the light beam can be substantially parallel to a spectacle lens plane which can extend parallel to a lens plane, for example.

In this case, the diffractive elements can be set up and arranged in such a way that the expanded light beam is a further collimated light beam and has an offset from the collimated light beam. This offset can be along the first main surface, substantially perpendicular to the direction of extent of the collimated light beam. This may have the advantage of the angle deflection for the beam shaping required by diffractive elements being present. This can improve the efficiency of the system.

In some devices, the at least one diffractive element can comprise a group of diffractive elements, each of which is configured to receive light from a respective reception direction and to deflect a first portion of said light in a respective deflection direction and to transmit a second portion of said light in a respective transmission direction. In this context, a first group element of the group of diffractive elements can be configured to receive light from the light source.

As a result, it may be possible to obtain a compact arrangement for illuminating the eye.

The expanded light beam can extend in at least one of the respective reception directions.

As a result, it may be possible to "connect" the individual group elements in a row and transmit the light firstly along the transmission direction (for example, along an imaginary x-axis) and partly deflect said light into the deflection direction (for example, in the direction of an imaginary y-axis).

The transmission direction and deflection direction, defined globally above, can be generalized to a plurality of transmission directions and deflection directions, for example locally in each case for individual deflection elements. As a result of this, it is possible to realize tree structures or relatively complex combinations of tree and series structures:

In some devices, the at least one diffractive element can comprise a group of diffractive elements, each of which is configured to receive light from a respective reception direction and to deflect a first portion of said light in at least one respective deflection direction and to transmit a second portion of said light in at least one respective transmission direction. In this context, a first group element of the group of diffractive elements can be configured to receive light from the light source.

As a result of this, it may be possible to transmit light in a tree structure in deflection directions and/or transmission directions. By way of example, the light can be transmitted in two transmission directions in each case, with the number of diffractive elements N being accompanied by a $2^N$ tree structure; however, other numbers of transmission directions and/or deflection directions are also possible. Additionally, series connections, in which the light is deflected and/or transmitted in exactly one direction in each case, can be combined with tree structure regions.

The group of diffractive elements can comprise a second group element. The latter can be arranged such that it transmits light in its transmission direction to a third group element in the reception direction of the third group element.

In this context, the device can be configured to output couple the light into the respective deflection direction toward the user.

As a result, the light can be distributed over a large area, which may improve the power supply of the active ocular implant.

The group of diffractive elements can be configured such that the respective ratio of the first portion to the second portion increases with the number of group elements of the group of diffractive elements that have been traversed by the light in the spectacle lens.

This may be advantageous in that a homogeneous illumination is achieved by the group elements by virtue of the reflectivity being raised with the number of elements traversed.

The optical arrangement can comprise at least one diffractive output coupling element. The latter can be configured to receive light from the at least one diffractive element and output couple said light to the user.

The at least one diffractive output coupling element can be configured to output couple the light to the user with effective focusing.

Effective focusing is understood to mean that the light from an imaginary emission surface is concentrated on an imaginary focus surface, with the imaginary focus surface being smaller than the imaginary emission surface. By way of example, the imaginary emission surface can be the first main surface of the spectacle lens. The imaginary focus surface can be arranged in the direction of the active ocular implant, for example an imaginary surface upstream of the pupil of the eye of the user.

By way of example, this can be achieved by focusing on a point. By way of example, this can also be achieved by focusing on a multiplicity of focus points lying close to one another. It can also be achieved by plane waves that run from different initial points toward a center. A combination of different variants is also possible, for example from different regions of the spectacle lens.

The effective focusing emanating from a large emission surface through the first main surface can improve the supply of the eye because, for example, the effectively focused light can reach the active ocular implant through the pupil opening for relatively large rotation angles of the eye. To this end, the light can be effectively focused on the pupil or on the center of rotation of the eye or on a point on the connecting line between pupil and center of rotation of the eye. However, other types of focusing are also conceivable.

The disclosure also includes a device for supplying power to an active ocular implant in an eye of a user. In certain embodiments the device comprises a spectacle lens with a first main surface and a second main surface, and comprises a light source and an optical arrangement.

The optical arrangement is configured to input couple light from the light source into the spectacle lens and output couple said light from the first main surface of the spectacle lens to the user. In this case, the optical arrangement comprises:

at least one diffractive deflection element which is configured to receive a light beam from a first direction and transmit said light beam in a second direction from a number of possible directions.

In this case, the second direction depends on:
an angle of incidence between the light beam and the at least one diffractive deflection element, and/or
a wavelength of the light beam, and/or
a switching state of the at least one diffractive deflection element.

Here, the switching state is understood to mean that the diffractive deflection element has different states that can be actively influenced, for example driven. By way of example, switching can be switched by means of an electro-optic process, wherein different deflection behaviors can be selected by way of a voltage that is applied to the diffractive element. In this case, switching can be continuous or discrete.

In cases where the at least one diffractive deflection element is a volume hologram the strongly pronounced wavelength selectivity and angle of incidence selectivity of volume holograms can be exploited. However, these effects may also be present in the case of other diffractive elements, possibly to a different extent, and may likewise be exploited.

The device as per the second aspect of the invention can be arranged like the device as per the first aspect of the invention.

The number of possible directions can be finite, for example defined on account of orders of diffraction in the form of angles of these orders of diffraction apart from an unsharpness. What can be exploited here is that diffractive elements may have different imaging functions as a function of wavelength and angle of the incident light.

The at least one diffractive deflection element may comprise a multiply exposed volume hologram. The number of possible directions can be based on the number of multiple exposures of the multiply exposed volume hologram.

Such deflection elements can be used in targeted fashion by variations in the light source, for example by means of scanning mirrors or by means of different, switchable light sources which illuminate different solid angles.

The at least one diffractive deflection element may comprise a first and a second diffractive deflection element, wherein the first and the second diffractive deflection element may be arranged at least partly separately in the spectacle lens and may each be configured to transmit light to the at least one diffractive output coupling element.

By way of example, this may be advantageous in that light can be provided to the same output coupling elements from different light sources and/or from different directions.

The at least one diffractive output coupling element may comprise a first output coupling element and a second output coupling element. In this case, the number of possible directions may comprise:
a direction from the at least one diffractive deflection element to the first output coupling element and
a direction from the at least one diffractive deflection element to the second output coupling element.

By way of example, the first output coupling element can be arranged in the upper region of a spectacle lens and the second output coupling element can be arranged in the lower region. If the user now gazes upward, the deflection element can be driven such that the light only reaches the first (upper) output coupling element and the active ocular implant in the eye of the user is supplied. There can be a switch if the user now gazes downward, and so the second output coupling element transmits light to the active ocular implant. Consequently, the power demands of the device can be reduced.

The at least one diffractive deflection element can be at least one volume hologram that is arranged in the spectacle lens.

A first deflection element of the at least one diffractive deflection element can be configured to convert the light beam into a divergent deflected light beam. As a result, the optical arrangement can be configured to emit the divergent deflected light beam into the second direction.

As a result, the light beam can be expanded. This can allow a small, compact input coupling optical unit, attached to a spectacle hinge for example, to nevertheless illuminate a large part of the spectacle lens. As a result, the required dimension of the light from the light source can be reduced, which may lead to the result of being able to reduce the weight of the device, for example by virtue of being able to design a possible collimator prism for beam shaping of the light source to be smaller.

According to the combination of the first and second aspect of the invention, an device is provided for supplying power to an active ocular implant in an eye of a user. In this case, the device is configured according to the first aspect of the invention and according to the second aspect of the invention.

In this case, the at least one diffractive element of the first aspect of the invention is arranged in at least one of the number of possible directions.

As an alternative or in addition thereto, the at least one diffractive deflection element comprises or is the at least one diffractive element. Expressed differently, the at least one diffractive deflection element of the second aspect of the invention can be realized by one or more diffractive elements as per the first aspect of the invention.

Various advantageous devices can be provided by this combination of first aspect of the invention and second aspect of the invention. Thus, the first aspect of the invention can be used to provide various diffractive elements in the second aspect of the invention.

At least one of the diffractive elements can be a volume hologram.

By way of example, diffractive elements may be: the at least one diffractive element, the at least one diffractive output coupling element, the at least one diffractive deflection element. However, other diffractive elements described above and below may also be embodied as volume holograms provided the description does not explicitly preclude this.

At least two of the diffractive elements can each be a volume hologram. In this case, one of the two diffractive elements can be a transmissive volume hologram and the other of the two diffractive elements can be a reflective volume hologram.

It may be possible to embody the device in more compact fashion by way of such combinations of transmissive and reflective volume holograms.

The first main surface and/or the second main surface may have at least one curve.

This may be advantageous in that the spectacle lens can be used for optical correction in the visible range, in a manner comparable to a conventional pair of spectacles. By way of example, the spectacle lens may have a convex or concave form. However, more complex forms are also possible, for example a free form or forms known from multifocal or progressive addition lenses.

The light source in certain embodiments may comprise at least one of the following elements:
  two individual light sources which are configured to provide light in different directions and/or in different wavelength ranges and/or at different illumination positions of at least one input coupling element of the optical arrangement,
  a beam splitter,
  a scanning mirror,
  a switchable element.

In this way it is possible to switch between different light distributions of the light, for example a light distribution for supplying power to the ocular implant and a light distribution for other purposes, or between different light distributions for supplying power to the ocular implant by virtue of the individual light sources, the beam splitter, the scanning mirror and/or the switchable element being driven accordingly.

Preferably, the switchover in this case is implemented on the basis of a line of sight of the eye, which is captured by an eye tracker for example. Thus, power can be efficiently supplied to the ocular implant in the respective line of sight. In this way, the ocular implant can also be supplied over a large field of view.

The spectacle lens may have a cutout. This can facilitate some examinations of the eye when the spectacles are worn.

The aforementioned features and those yet to be explained be—low can be used not only in the respectively specified combination but also in other combinations or on their own, without departing from the scope of the present invention.

BRIEF DESCRIPTION OF THE DRAWINGS

Below, the invention will be explained in detail by way of exemplary embodiments, with reference being made to the attached drawings. In the drawings:

FIGS. 12, 13 and 14 show different devices according to different exemplary embodiments with groups of diffractive elements, output coupling elements and a beam expansion optical unit.

DETAILED DESCRIPTION

Various exemplary embodiments are explained in detail below. These exemplary embodiments are only illustrative and should not be construed as restrictive. For example, a description of an exemplary embodiment with a multiplicity of elements or components should not be construed as meaning that all of these elements or components are necessary for implementation. Rather, other exemplary embodiments also may contain alternative elements or components, fewer elements or components or else additional elements or components. Elements or components of different exemplary embodiments can be combined with one another, unless stated otherwise. Modifications and variations which are described for one of the exemplary embodiments can also be applicable to other exemplary embodiments.

In order to avoid repetition, the same elements or corresponding elements in various figures are denoted by the same reference sign and are not explained a number of times.

The figures are geared towards illustrating the underlying principles. Surface shapes and refractions, for example, may therefore be indicated schematically. By way of example, refractions may be illustrated in exaggerated fashion or may be neglected.

The described techniques are applicable to a multiplicity of different active ocular implants, as mentioned at the outset.

Various devices for supplying power to an ocular implant are described below in exemplary fashion. In this case, known devices are compared to devices according to the invention in particular.

Figure 1A:
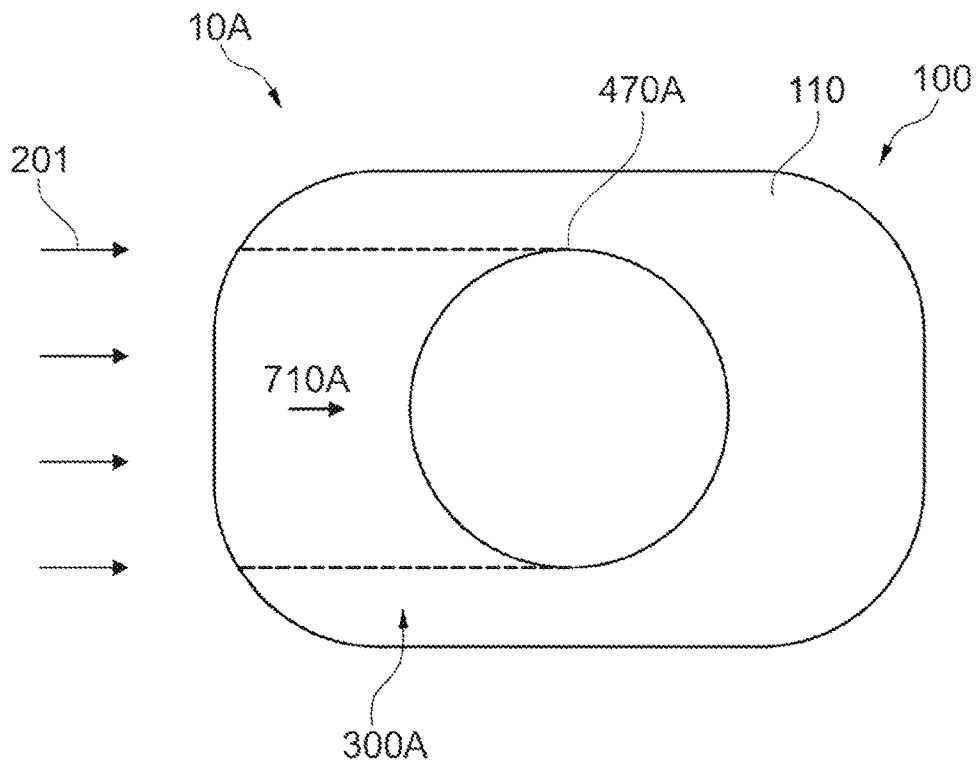
FIG. 1A shows an device known from the prior art.

FIG. 1A shows an device 10A known from the prior art. The device 10A comprises a spectacle lens 100 with a first main surface 110. In this case, the main surface 110 faces a user of the device 10A when the latter wears the device, which may be installed in a spectacle frame for example. The spectacle lens 100 is configured to guide a collimated light beam 210 to an output coupling hologram 470A in a direction 710A. The output coupling hologram 470A provides the light for the user, who is wearing an active ocular implant in the eye associated with the spectacle lens 100.

Figure 1B:
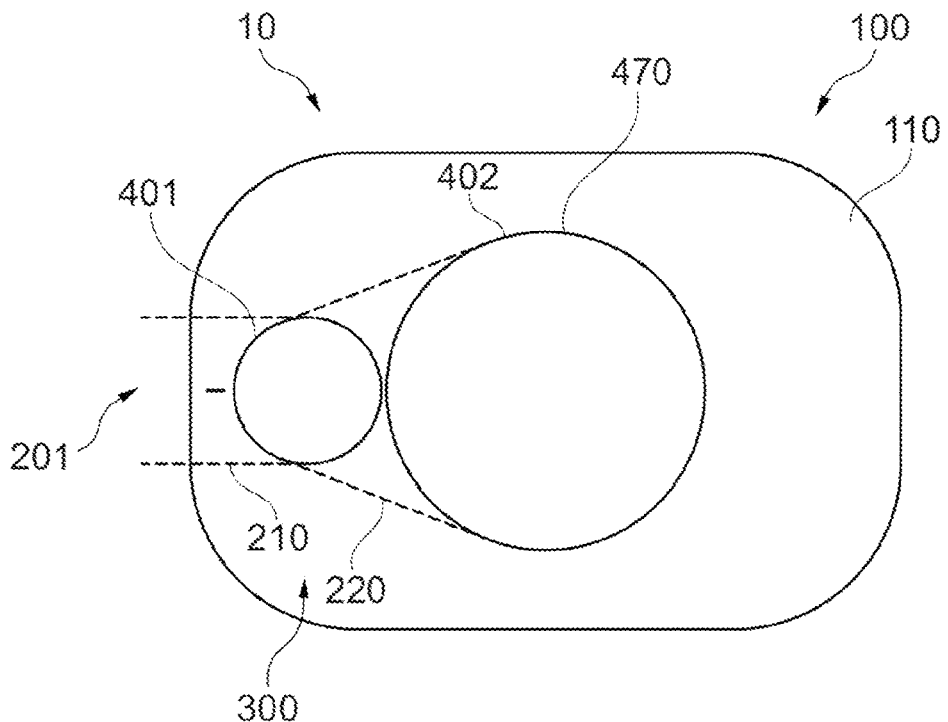
FIG. 1B shows a device according to an exemplary embodiment.

FIG. 1B shows an device 10 according to an exemplary embodiment that shows a development of the device 10A of FIG. 1A. The spectacle lens 100 of FIG. 1B is also configured to receive a collimated light beam 201. In contrast to the collimated light beam of FIG. 1A, the collimated light beam 201 of FIG. 1B can be significantly narrower. The light beam is received by a first diffractive element 401. In this case, the first diffractive element 401 can be arranged obliquely in the spectacle lens 100.

The diffractive element 401 is configured to receive the collimated light beam and provide the latter as a divergent light beam 220. The divergent light beam 220 is now transmitted to a second diffractive element 402. The second diffractive element 402 receives the divergent light beam 220 and provides an expanded light beam. In the shown example of FIG. 1B, the second diffractive element 402 is a diffractive output coupling element 470, which output couples the expanded light beam from the spectacle lens 100 and provides said expanded light beam for a user.

Figure 2:
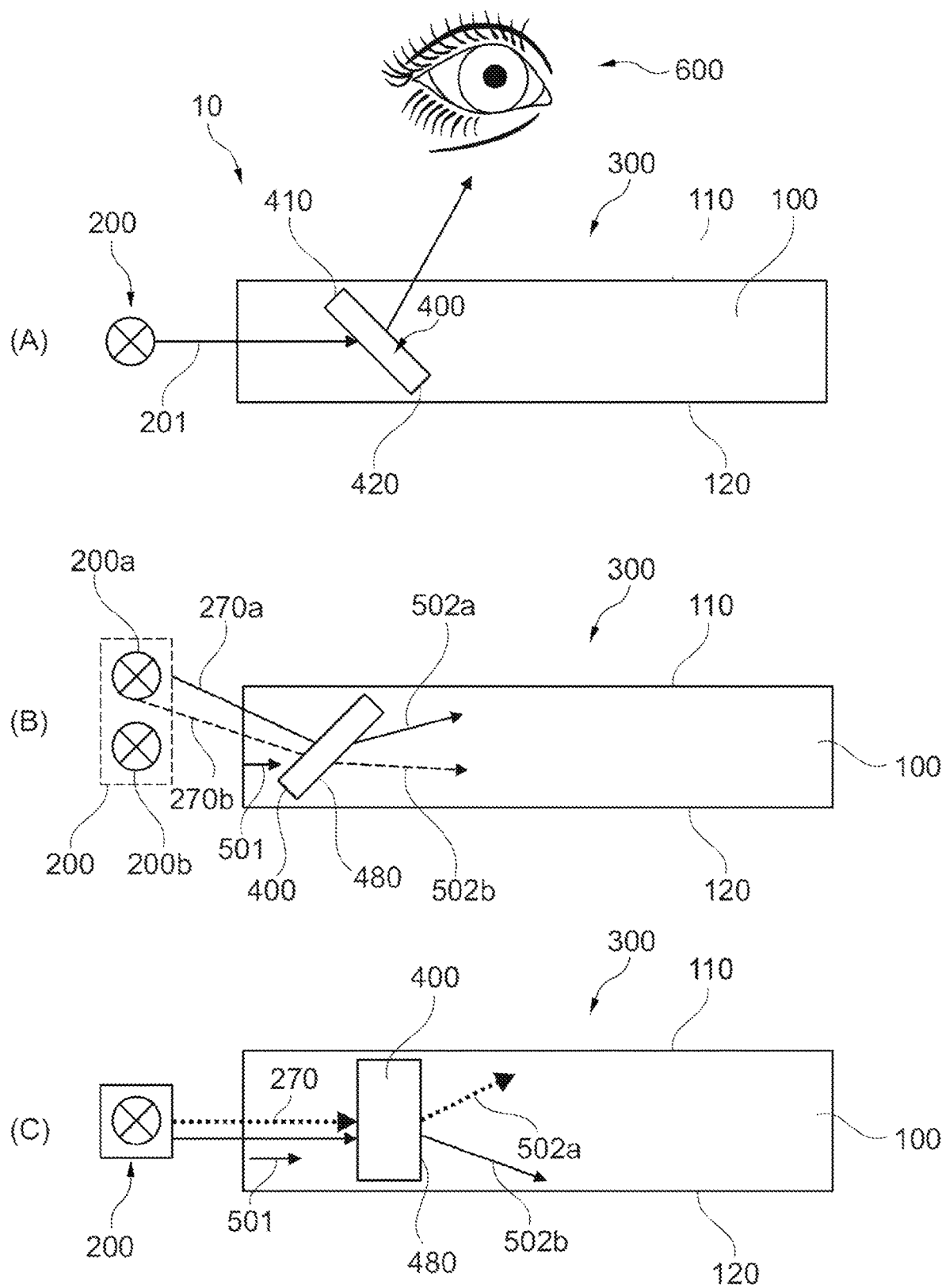
FIG. 2 shows different devices according to various exemplary embodiments.

FIG. 2 shows different devices according to various exemplary embodiments. Figures (A), (B) and (C) in FIG. 2 each show a side view of the spectacle lens 100. This spectacle lens can be the spectacle lens of FIG. 1B. The shown spectacle lenses 100 have a first main surface 110 that faces the user 600 and a second main surface 120 that faces away from the user 600. A light source 200 provides light 201 for a diffractive element 400.

FIGS. 2A, 2B, 2C show various exemplary embodiments of devices 10 for supplying power to an active ocular implant in an eye of a user 600, which comprise different optical arrangements 300.

FIG. 2A shows a diffractive element 400 with a first end 410 and a second end 420. The diffractive element 400 is buried obliquely in the spectacle lens 100 such that the first end 410 has a different distance from the first main surface 110 than the second end 420. The spectacle lens 100 in the shown example is a planar spectacle lens, i.e., a spectacle lens without refractive power. In other exemplary embodiments the spectacle lens might also have one or more curved main surfaces and the diffractive element 400 may be arranged accordingly obliquely in relation to the curved surfaces, for example a selected curved surface.

FIG. 2B shows an extended light source 200. This is indicated schematically by two different light sources 200a and 200b. In the exemplary embodiment of FIG. 2B, the diffractive element 400 is a diffractive deflection element 480. On account of the extent of the light source 200, the respective light rays of the light source 200a and 200b reach the diffractive deflection element 480 at different angles of incidence between the light beam 270a, 270b and the diffractive deflection element 480. The diffractive deflection element 480 is configured to transmit the light in a second direction 502a, 502b, wherein the second direction in the example of FIG. 2B depends on the angle of incidence and is accordingly different for the two light sources 200a, 200b.

FIG. 2C shows a light source 200 that is configured to provide light with different wavelengths. Two different wavelengths are shown in exemplary fashion, one as a full line and the other as a dotted line. In FIG. 2C, the light beam 270 provided by the light source is also received by the diffractive element 400 from a first direction 501. In the exemplary embodiment of FIG. 2C, the diffractive element 400 is likewise a diffractive deflection element 480 which is configured to transmit the light beam 270 in a respective second direction 502a, 502b on the basis of a wavelength of the light beam 270.

Figure 3A:
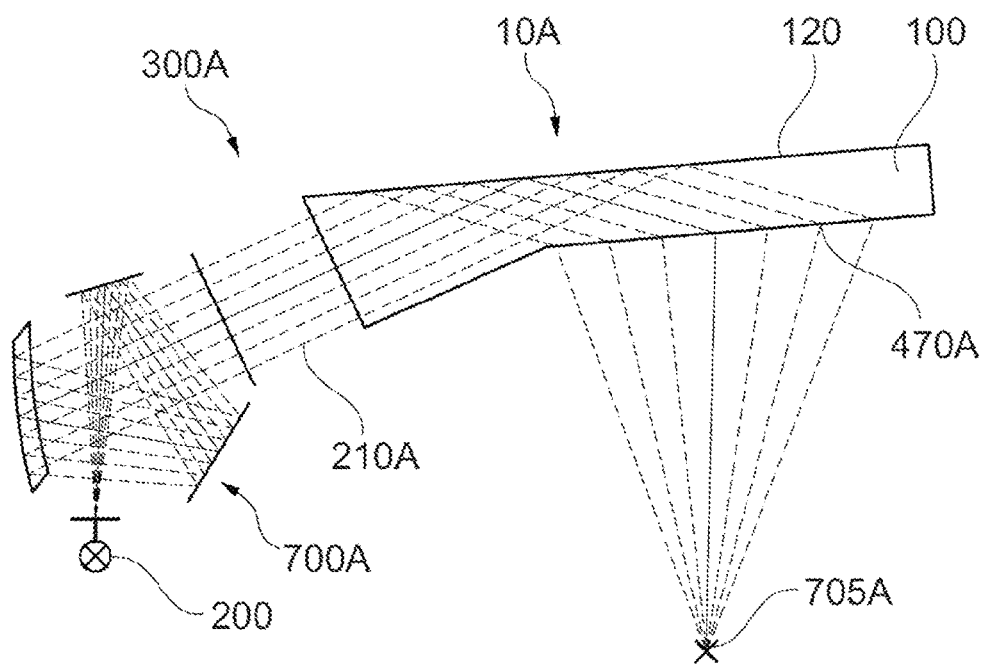
FIGS. 3A and 3B show a device known from the prior art.
Figure 3B:
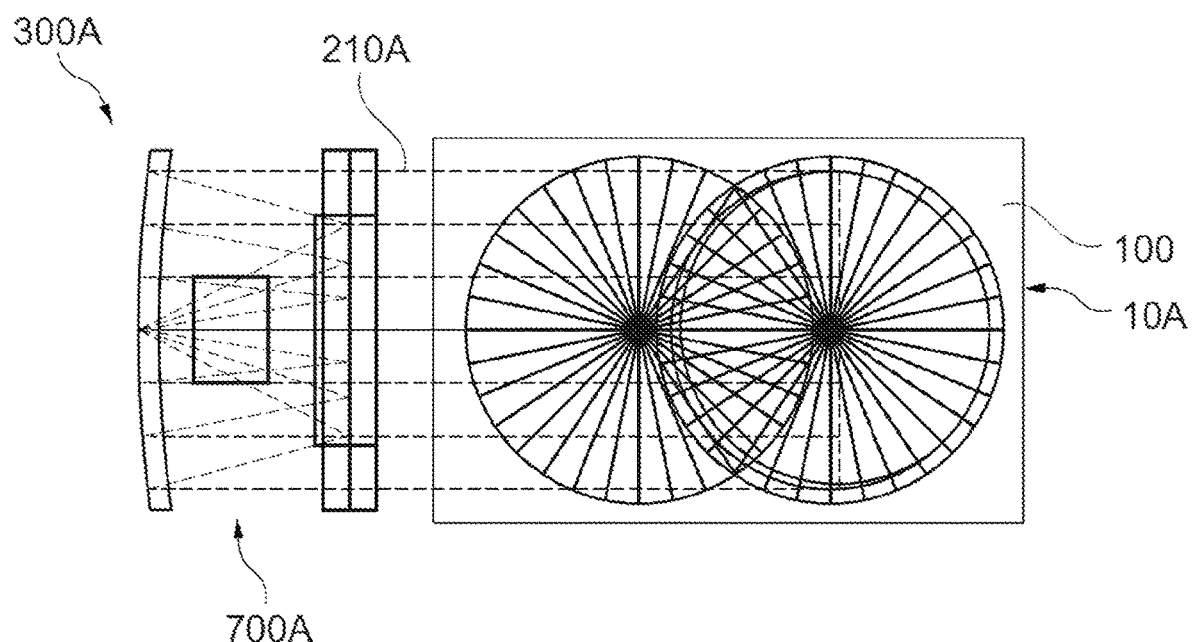

FIGS. 3A and 3B show an device 10A which is known from the prior art for supplying power to an active ocular implant in an eye of a user. FIG. 3A shows a lateral view while FIG. 3B shows a plan view of an optical arrangement 300A of the device 10A. A light source 200 transmits light which is shaped into a collimated light beam 210A by a collimator prism 700A. The collimated light beam 210A enters into a spectacle lens 100 and experiences total-internal reflection at the second main surface 120 of the spectacle lens 100 and thus reaches an output coupling element 470A which is embodied as a surface hologram. The second main surface 120 may also be embodied as a hologram. The output coupling element 470A provides a focused light beam with a focal point 705A for the user. The focal point 705A can be located in a pupil plane of a user, for example. The extent of the beam for the user is determined by the height of the surface hologram in this case.

Figure 3C:
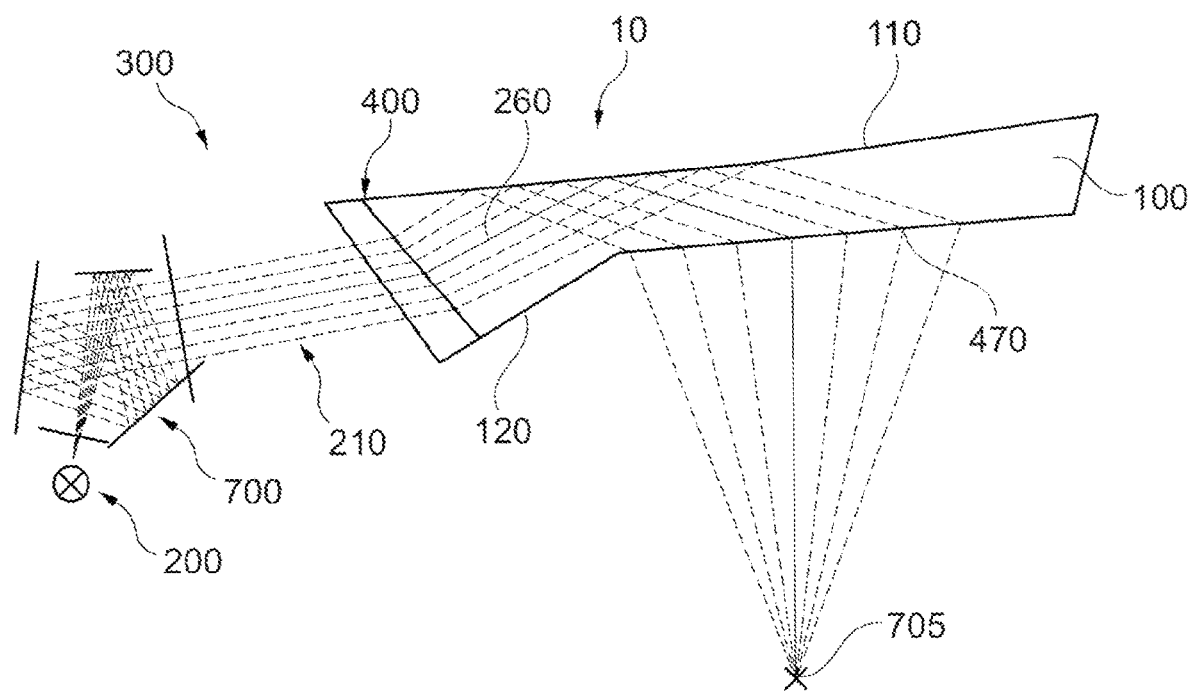
FIGS. 3C and 3D show a device according to an exemplary embodiment.
Figure 3D:
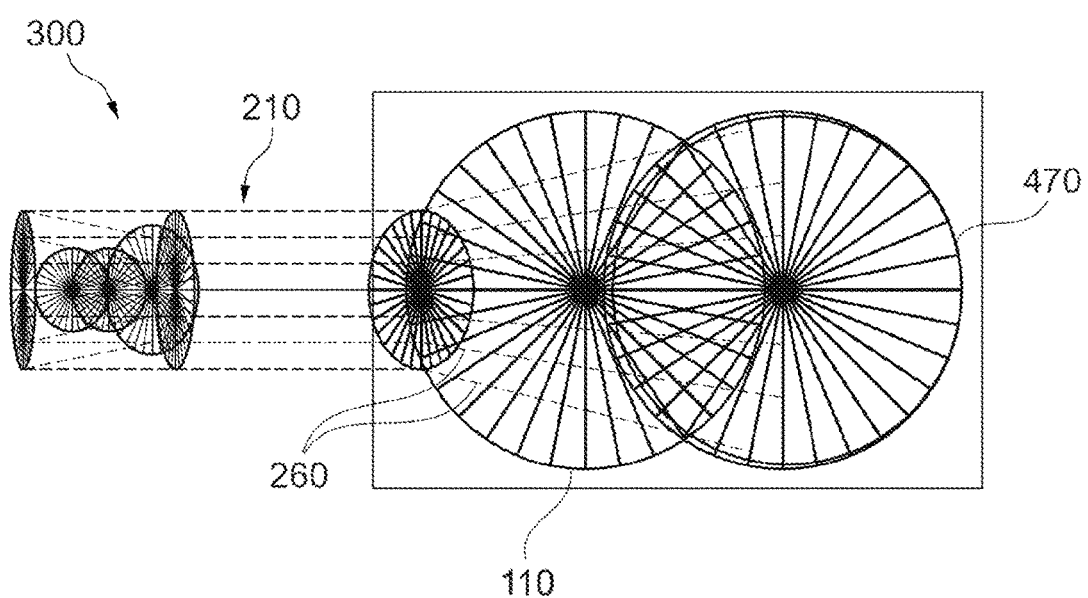

FIGS. 3C and 3D show a development of the device in FIGS. 3A and 3B according to various exemplary embodiments. FIG. 3C likewise shows a lateral view of an optical arrangement 300 of an exemplary embodiment according to the invention, which may be part of an device 10 according to the invention for supplying power to an active ocular implant in an eye of a user, and FIG. 3D shows a lateral view.

The device of FIGS. 3C and 3D also comprises a collimator prism 700, although the latter is significantly smaller than the collimator prism 700A in FIG. 3A. Accordingly, the collimated light beam 210 provided by the collimator prism 700 is narrower than the collimated light beam 210A of FIG. 3A. In the spectacle lens 100, the collimated light beam 210 strikes a diffractive element 400 which is embedded in the spectacle lens 100 and which may be embodied as a volume hologram. The diffractive element 400 expands the light beam and provides an expanded light beam 230 which undergoes total-internal reflection at the second main surface 120 of the spectacle lens 100 and which is guided to a diffractive output coupling element 470. The latter focuses the light on a focal point 705. Like in the example of FIG. 3A, the focal point in FIG. 3C may also be located in a pupil plane of the user, for example.

The optical arrangement 300 in FIGS. 3C and 3D may have various advantages. As a result of the volume hologram embedded obliquely in the spectacle lens it is possible to provide a beam with the same extent, in some cases even with a greater extent, to the user despite using a collimator prism 700 with a smaller volume in comparison with the collimator prism 700A of FIG. 3A. As a result, the volume required for an device for supplying an active ocular implant can be reduced, possibly improving comfort of wear and esthetics.

As a result of embodying the diffractive element 400 as a buried diffractive element 400, it is easier to ensure the safety of the eyes from excess brilliance of the light source, for example in cases where the light source 200 is a laser light source. The entire optical structure 300 or parts thereof, for example the spectacle lens 100 and the collimator prism 700, can be produced in one piece in this case; this may be advantageous for the safety of the eyes, for example because stray light can be avoided at material transition points and/or because adhesive bonding minimizes the risk of separation between the different optical parts.

Figure 4:
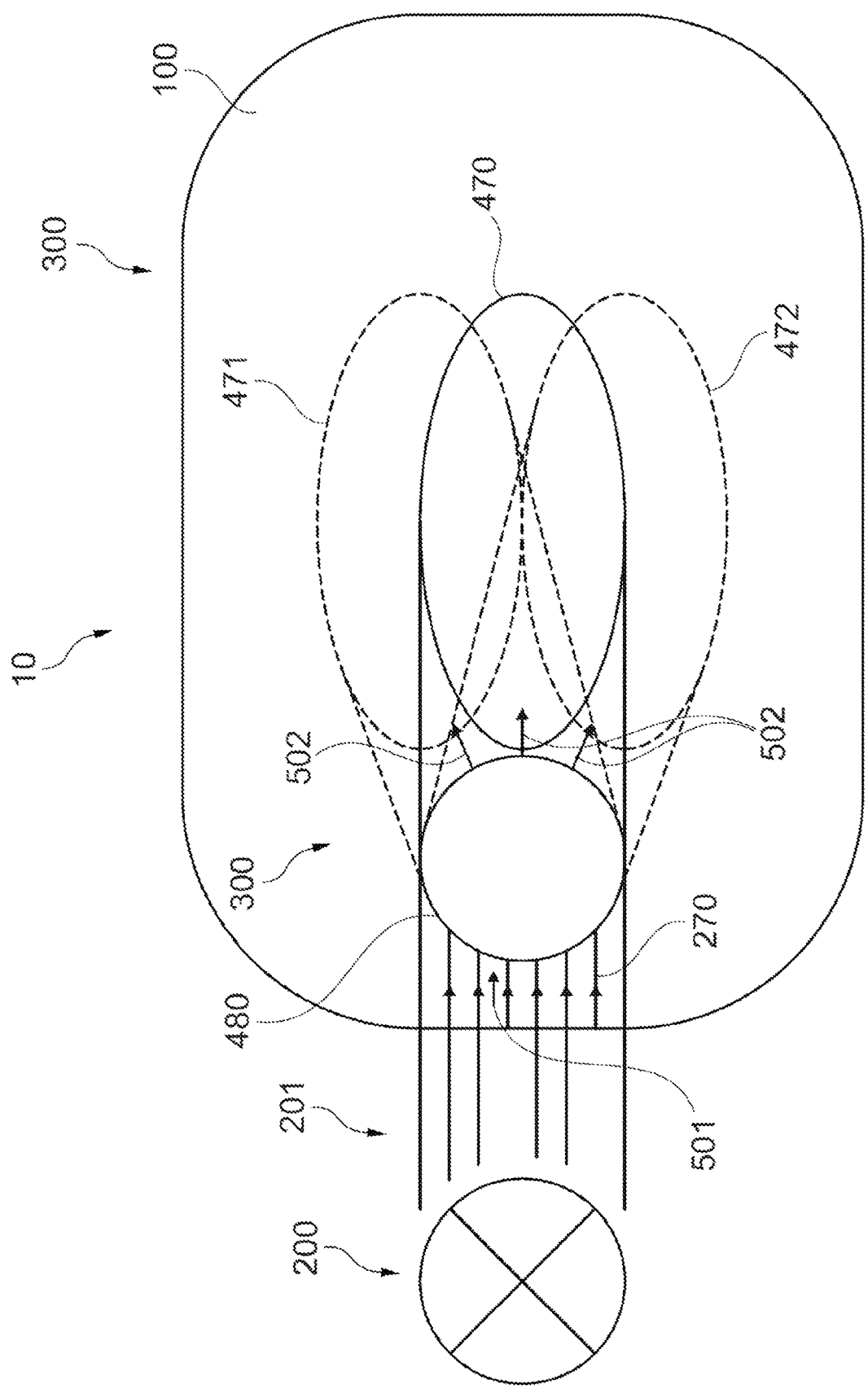
FIG. 4 shows a device according to an exemplary embodiment with a deflection element.
Figure 5:
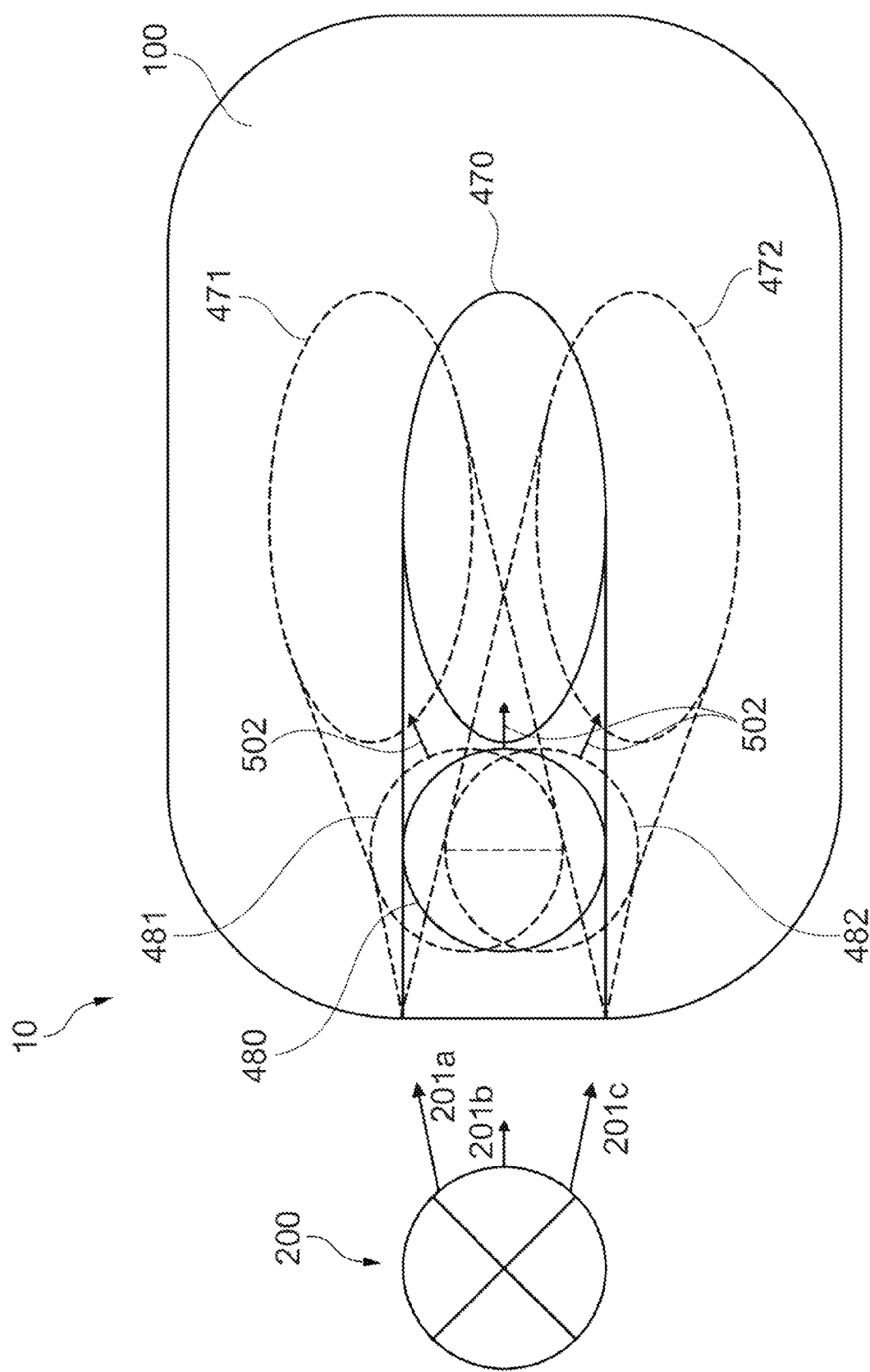
FIGS. 5 and 6 show further exemplary embodiments with deflection elements.
Figure 6:
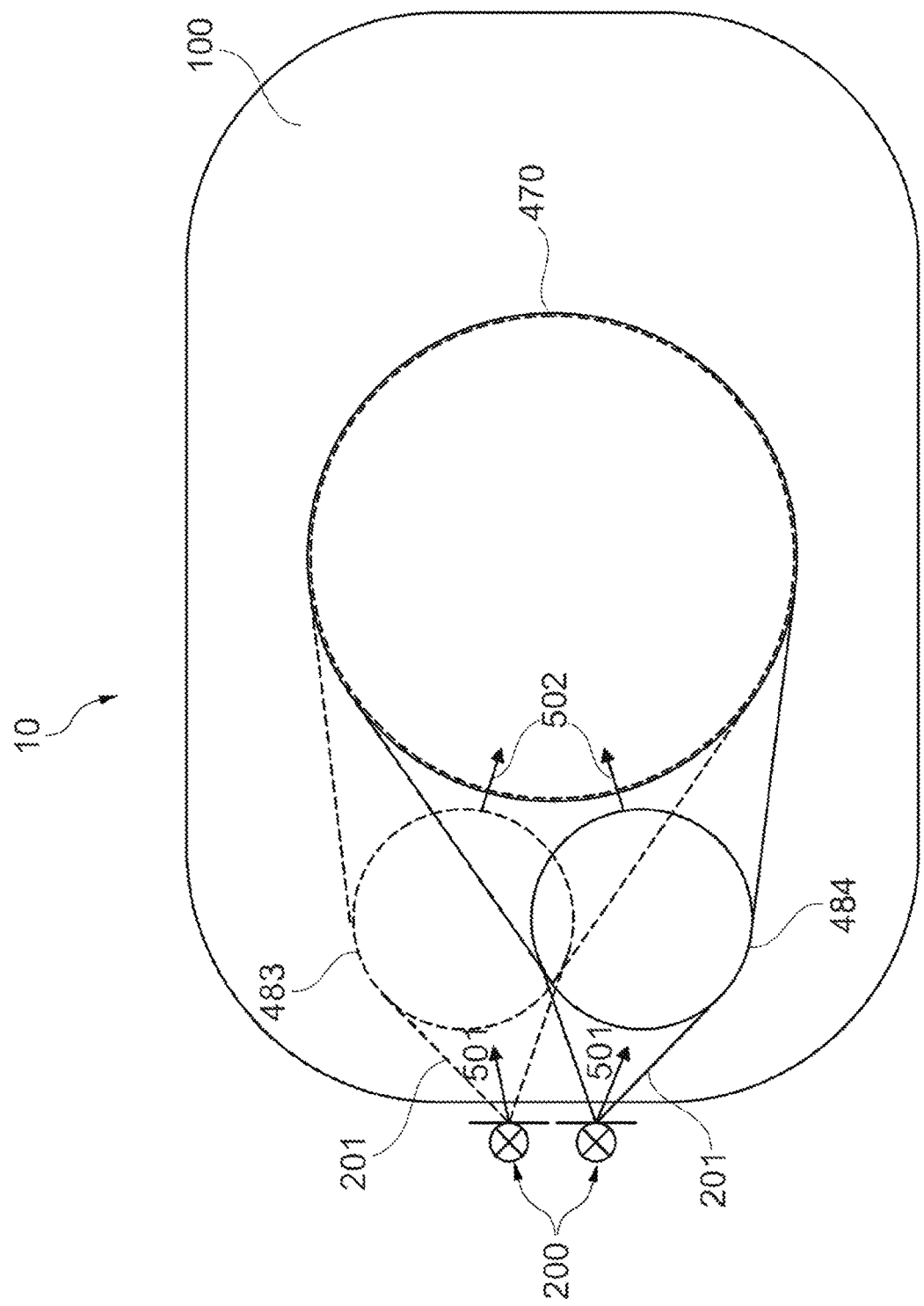

Further possible configurations of devices with diffractive elements arranged in a spectacle lens are explained below in conjunction with FIGS. 4-6. FIGS. 4-6 each show a spectacle lens 100 according to various exemplary embodiments of the device 10, said spectacle lenses receiving light 201 from a light source 200. In the exemplary embodiments of FIGS. 4-6, the light 201 is received by at least one diffractive deflection element 480, 481, 482 from a first direction 501 and transmitted in a second direction 502.

In the exemplary embodiment of FIG. 4, the diffractive deflection element 480 is embodied as a switchable diffractive deflection element. The diffractive element 480 has three different discrete states in the example shown. In each of the three states, the light beam 270 is received by the deflection element 480 from a first direction 501 and transmitted in a respective switching-state-dependent second direction 502. The optical arrangement 300 comprises three diffractive output coupling elements 470, 471, 472. In the shown exemplary embodiment of FIG. 4, these are arranged with an overlap in the volume of the spectacle lens 100. The output coupling elements 470, 471, 472 transmit the light to the active ocular implant of the user. By way of example, if the user gazes upward, this can be detected by a controller of the device 10 and the switchable deflection element 480 can be switched so that the second direction 502 is in the direction of the first output coupling element 471. As a result, the light can reach the active ocular implant well when the user gazes upward. If the user gazes downward, the deflection element 480 can be switched accordingly such that the deflected light beam reaches the output coupling element 472 and, as a result, the light can reach the active ocular implant well through the pupil. If the user gazes along zero line of sight, the diffractive deflection element 480 can be switched such that the light reaches the output coupling element 470 and hence can reach the active ocular implant in the eye of the user well. By way of example, this may be advantageous in that less light is unable to pass through the pupil opening, for example less light is shadowed by the iris. Expressed differently, "wasting" of light as a result of not even reaching the active ocular implant can be avoided.

This can reduce the luminous power that needs to be provided at a given time, possibly improving the energy efficiency of the device 10.

In FIG. 5, the light source 201 provides the light collimated in different directions for different deflection elements 480, 481, 482. These deflection elements 480, 481, 482 can be arranged in the same volume or at least with partial overlap in the volume of the spectacle lens 100. The deflection elements 480, 481, 482 are angle-selective.

Hence, depending on the direction of the light 201A, 201B, 201C from the light source 200, the light is transmitted in a narrow acceptance range from in each case only one of the deflection elements 480, 481, 482 to one of the output coupling elements 470, 471, 472 in the respective second direction 502. As a result, by controlling the angle of incidence, for example by way of an optical unit between the light source 200 and the spectacle lens 100, it is possible to supply light to only one or else more of the output coupling elements 470, 471, 472 in a targeted fashion. As a result, it is likewise possible to increase the energy efficiency of the device and/or use other light sources with different collimation characteristics, which may likewise increase the energy efficiency and/or reduce requirements in respect of installation space.

FIG. 6 shows a further exemplary embodiment. In the example of FIG. 6, the light source 200 provides light with different wavelength ranges in different directions 501. The respective light is guided by the diffractive deflection elements 480, in each case in the direction of an individual output coupling element 470 into the respective direction 502. This may be advantageous in that different light sources 200 can be used and a compact input coupling optical unit can be provided since the diffractive deflection elements 480 can overlap at least in part in the volume of the spectacle lens 100.

Figure 7:
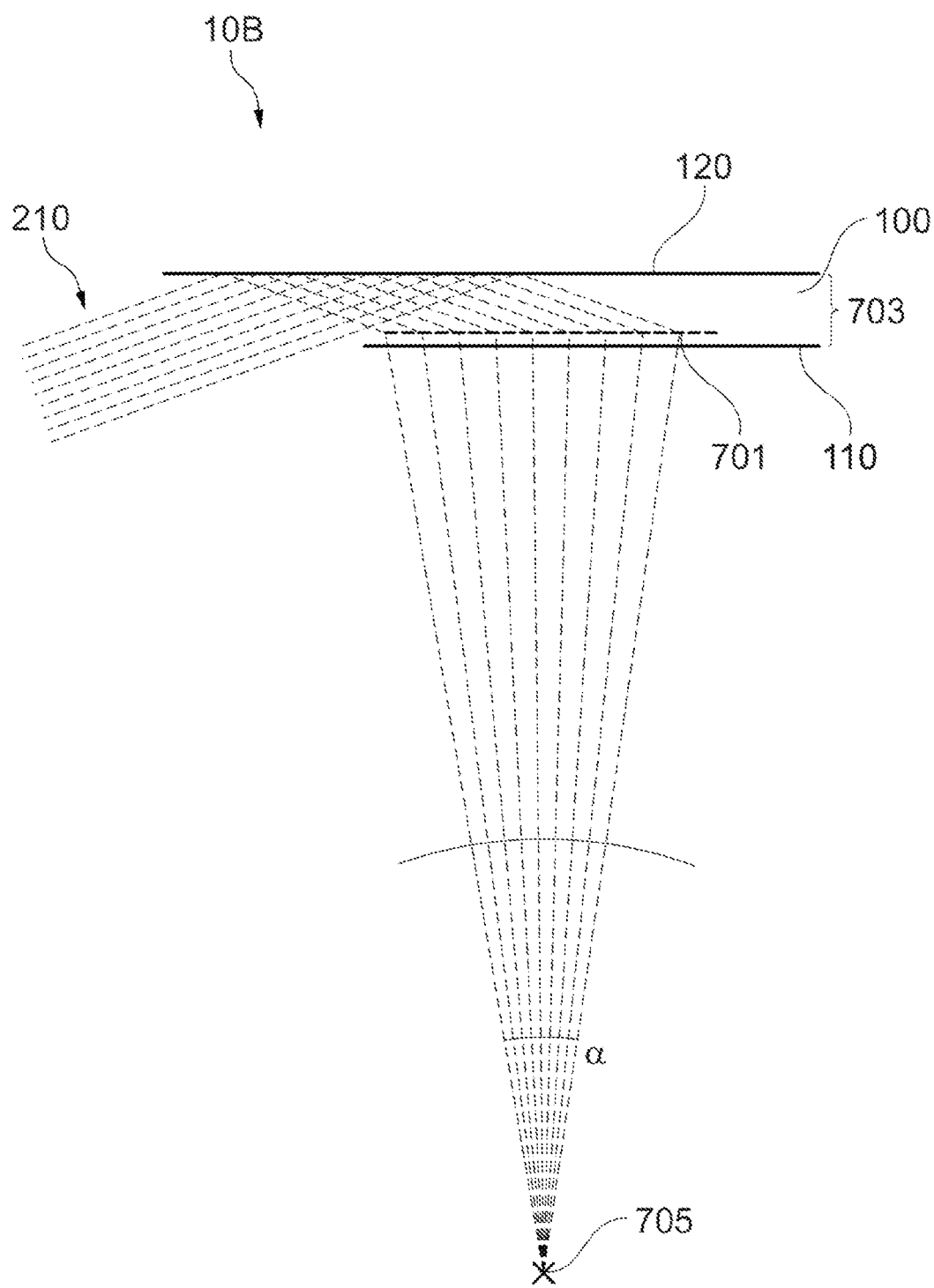
FIGS. 7, 8 and 9 show various devices known from the prior art.
Figure 8:
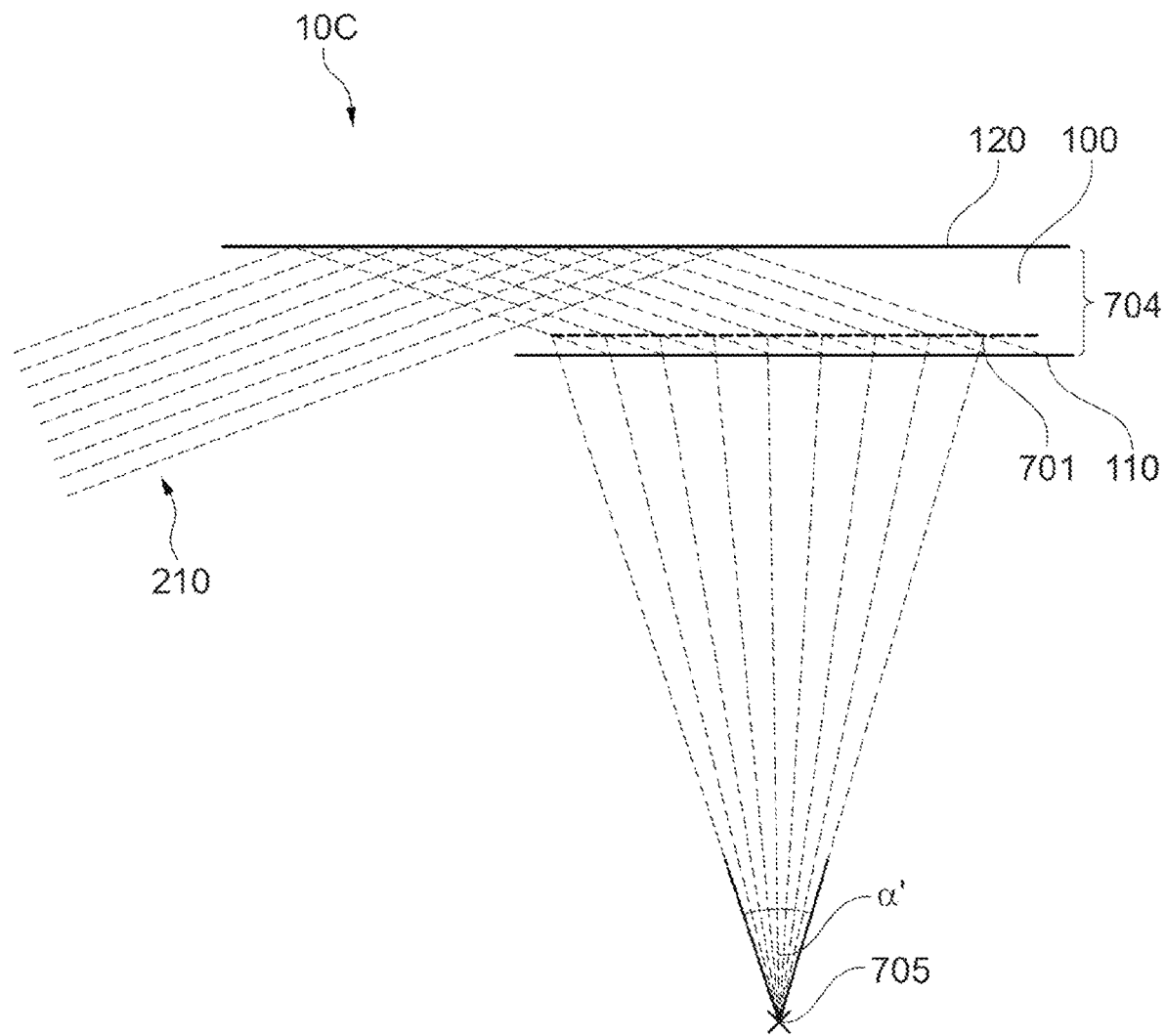
Figure 9:
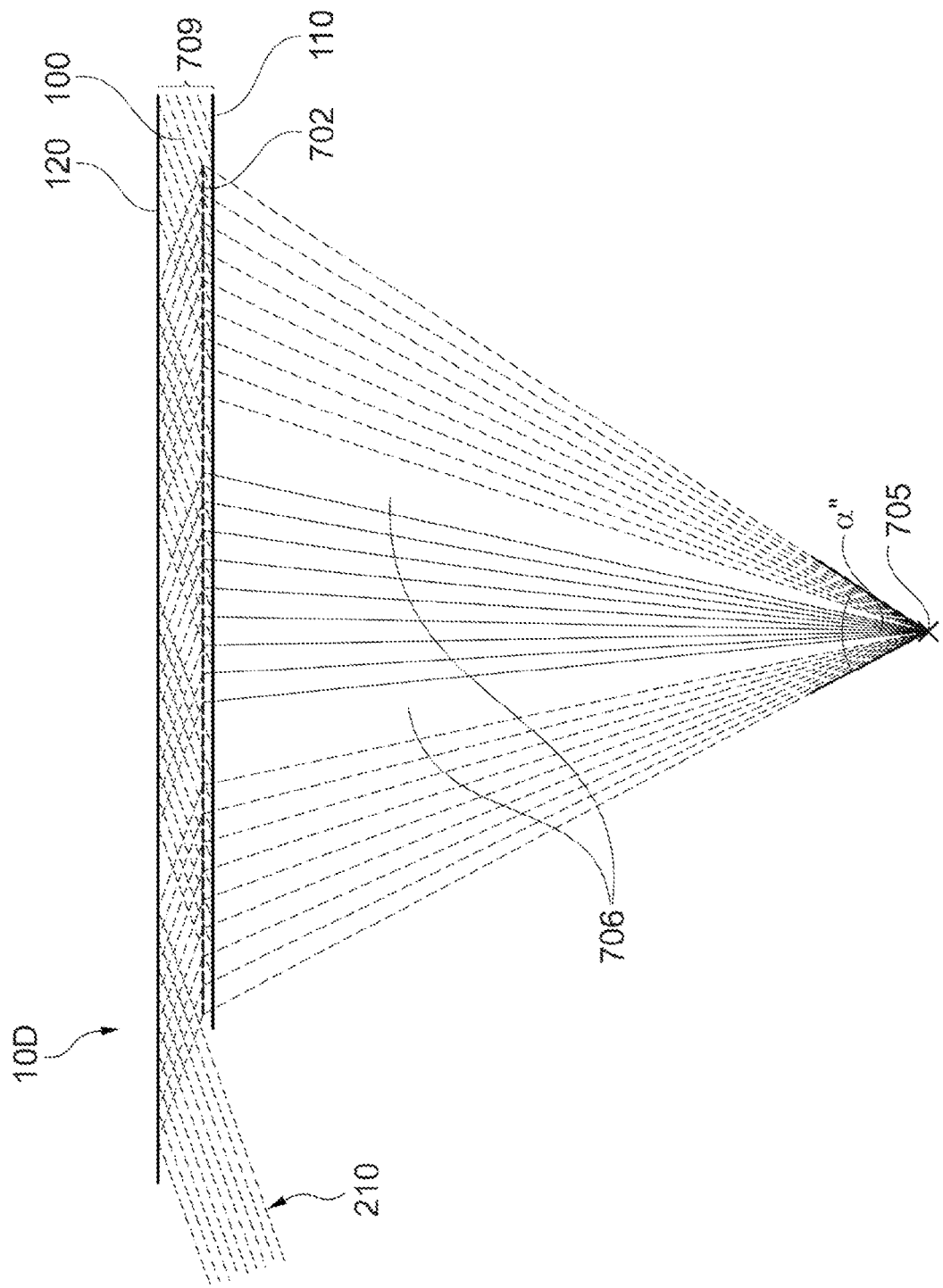

FIGS. 7, 8 and 9 elucidate conventional devices for supplying active ocular implants. Apart from the described details, this device can correspond to the device 10A from FIG. 3A and FIG. 3B.

To allow the user to gaze as freely as possible in different directions, it is necessary for light to reach the active ocular implant even in the case of different rotational positions of the eye. To this end, it is advantageous if the light reaches the focal point 705 from an angular range α, α', α" that is as large as possible. This angular range is sometimes also referred to as aperture angle of the device.

At the same time, it is desirable to keep the thickness 703, 704, 709 of the spectacle lens 100 low.

FIG. 7 shows an device 10B from the prior art, for example it could be the device 10A of FIG. 3A. In this case, the collimated light beam 210 is focused on the focal point 705 by a diffractive surface element 701 following total-internal reflection at the second main surface 120 of the spectacle lens 100. As a matter of principle, only a certain angle α can be attained for a given thickness 703 of the spectacle lens 100.

FIG. 8 shows an device 10C from the prior art. This device 10C renders it possible to increase the angle α of the device 10C in FIG. 7 to a greater angle α'. To this end, it is necessary to increase the diameter of the collimated light beam 210. What follows necessarily in the device 10A is that the thickness 704 of the spectacle lens 100 needs to be increased from the thickness 703 in order to be able to ensure a greater angle α'. A spectacle lens with the thickness 703, 704 of 4 to 5 mm is required in the prior art to realize aperture angles of 40°.

FIG. 9 shows a further device 10D according to the prior art. It is based on a collimated light beam 210 with a smaller diameter and a thinner spectacle lens 709 but simultaneously offers a greater aperture angle α" at the focal point 705. What this achieves is that the spectacle lens 100 is used with multiple total-internal reflection as an optical waveguide. Output coupling is implemented by a diffractive surface element which is arranged along the first main surface 110 of the spectacle lens 100. On account of geometric restrictions when input coupling into the spectacle lens 100, gaps 706 necessarily but undesirably occur along the multiple output coupling sites in the prior art.

A further challenge consists of devices for supplying active ocular implants often requiring the collimated light beams 210 to be provided from a fixed angular range. Since the output coupling diffractive elements 702 only have a very small angle acceptance range, the arising gaps 706 may be even more problematic since these may lead to supply problems and, in the worst case, to functional outages in the case of implants with small dimensions.

Figure 10:
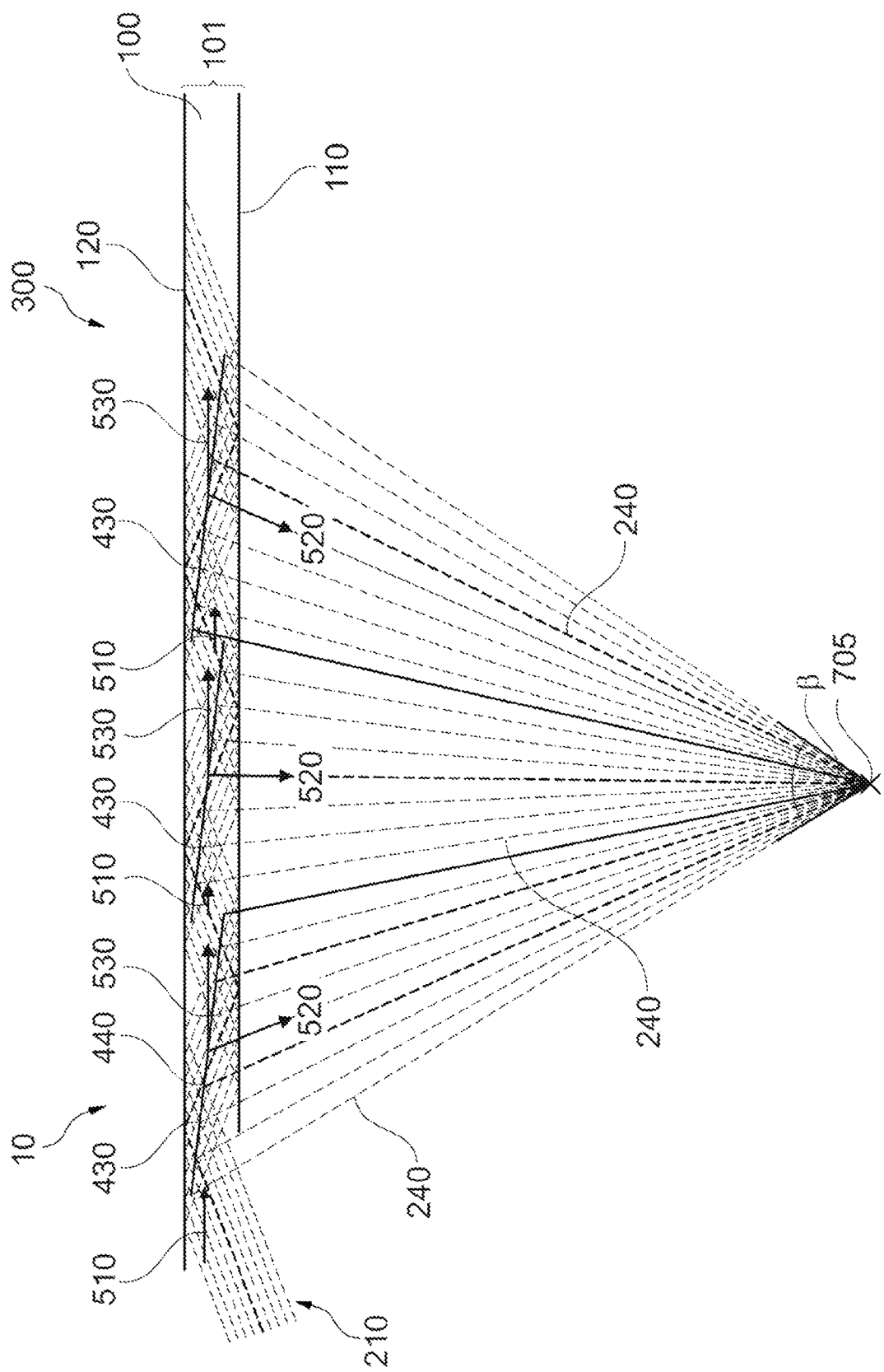
FIGS. 10 and 11 show different devices according to different exemplary embodiments with groups of diffractive elements.
Figure 11:
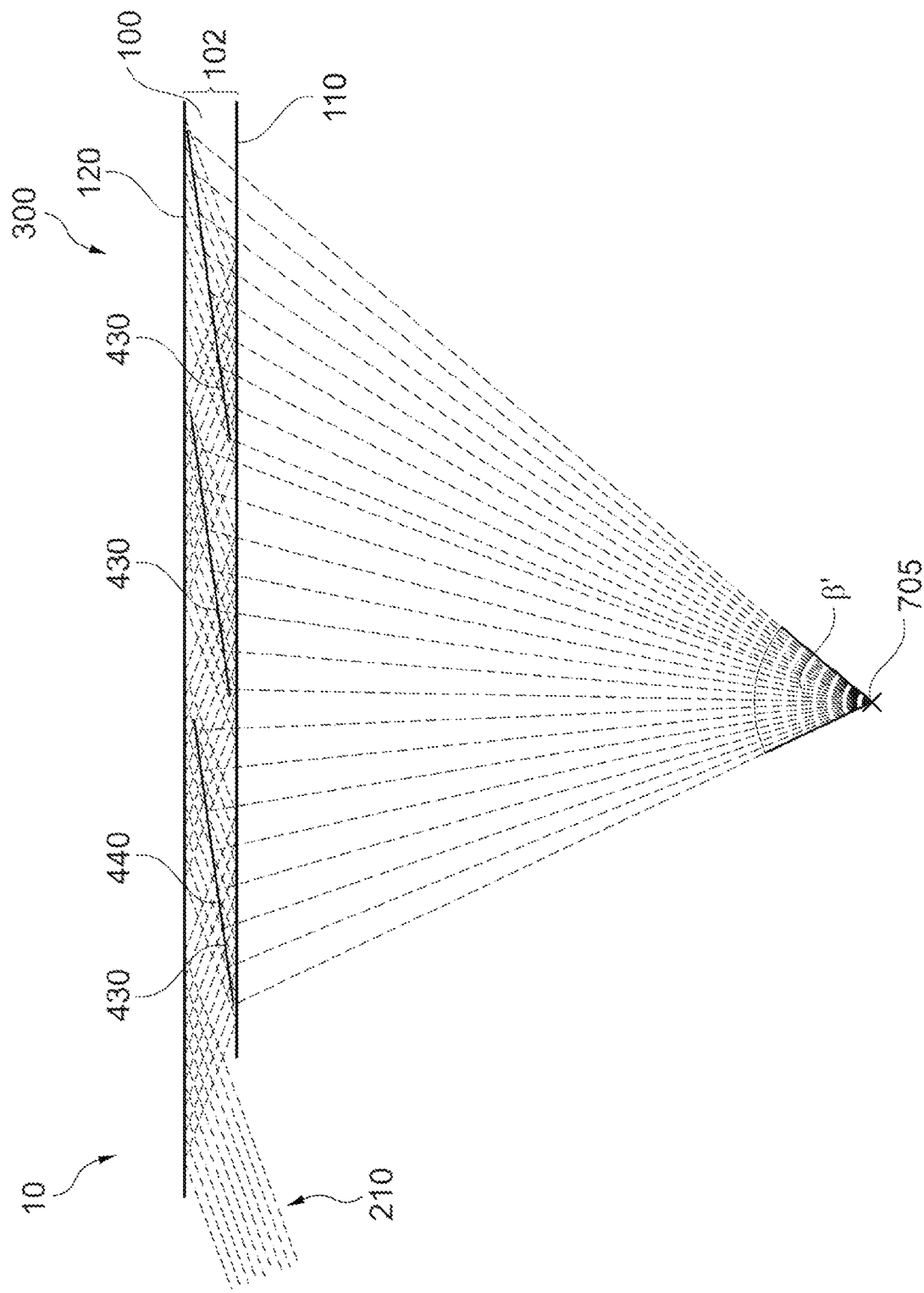

FIGS. 10 and 11 show two different exemplary embodiments of devices according to various exemplary embodiments. It is evident from the figures that a collimated light beam 210 is likewise input coupled into the spectacle lens 100. The latter has a thickness 101, 102 that is smaller than the thickness 704.

In the spectacle lens 100, a group of diffractive elements 530 is buried and arranged in inclined fashion in relation to the spectacle lens in each case. In each case, a first group element 440 is configured to receive the collimated light 210 from the light source.

Each of the diffractive elements from the group of diffractive elements 430 is configured to receive the light 201 from a first direction 510 and to deflect a first portion of said light in a respective deflection direction 520 and to transmit a second portion of said light in a respective transmission direction 530. In this case, the light is transmitted in the respective transmission direction 530 by total-internal reflection. As a result of this arrangement, a large angle β can be attained in some exemplary embodiments without gaps 706 occurring in the deflected light 240 or with said gaps at least being reduced. In FIG. 10, the group of diffractive elements 430 contains buried transmissive volume holograms. FIG. 11 illustrates an arrangement similar to that of FIG. 10. In the exemplary embodiment of FIG. 11, the group of diffractive elements 430 are, by contrast, embodied as buried reflection volume holograms.

The respective diffractive elements of the group of diffractive elements 430 can be embodied along the light path in such a way that the ratio of transmission and deflection changes in each case so that the same light intensity is attained over the illumination angle β and β'.

This principle can also be used in other arrangements; by way of example, in cases with more than one light source, for example one light source per side, the ratio of transmission and deflection can be changed accordingly element-by-element, in each case toward the center of the spectacle lens 100, along the respective transmission light path.

The combination—not shown—of buried reflection and transmission holograms is also possible.

Such groups of diffractive elements can also form a tree structure. Such an device 1100 is illustrated in FIG. 15.

Figure 15:
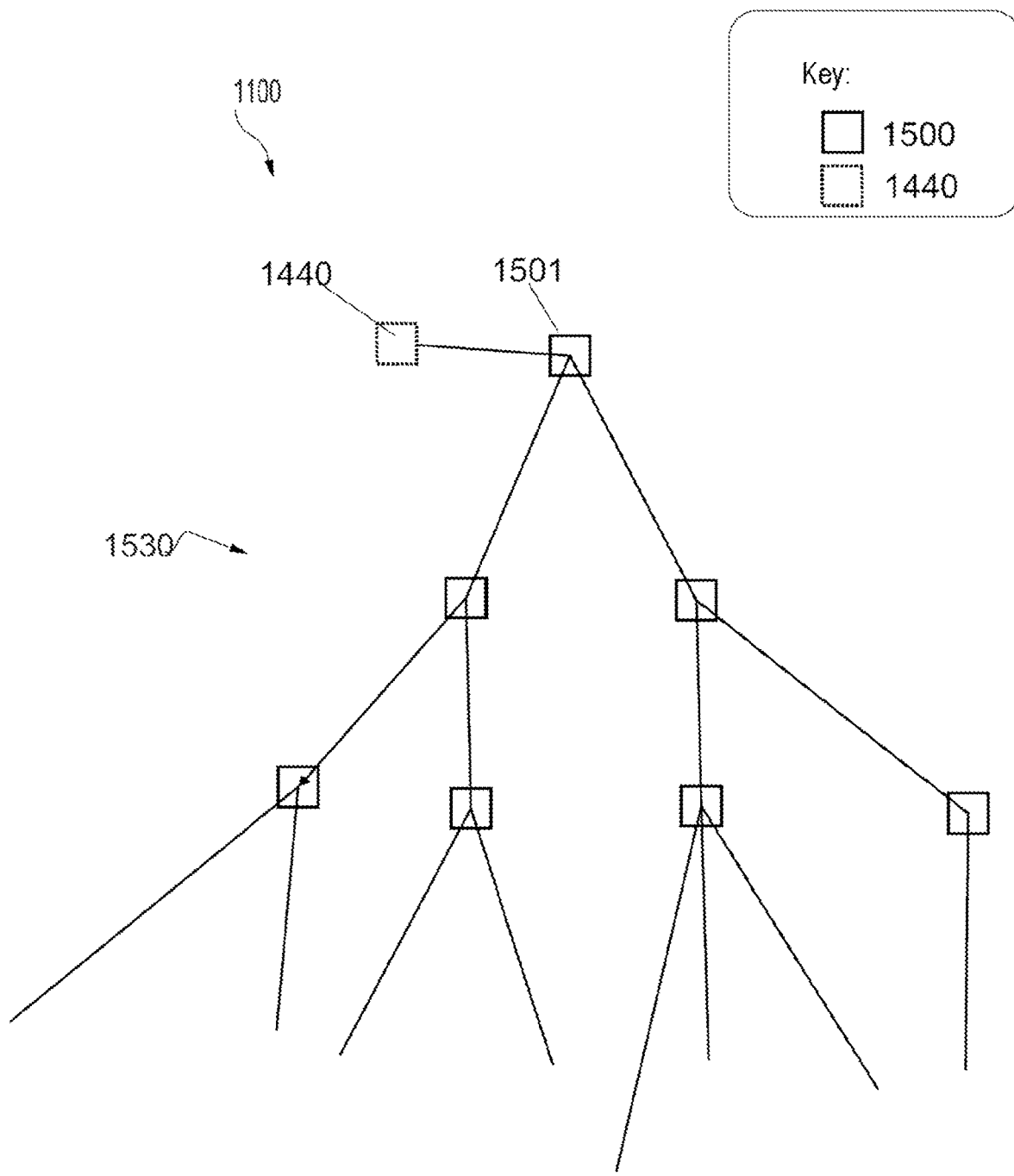
FIG. 15 is a diagram for elucidating a tree structure in some exemplary embodiments.

FIG. 15 in this case shows a detailed view of an device 1100 which, as described for the exemplary embodiments above, is arranged in a spectacle lens that serves as an optical waveguide. A multiplicity of diffractive elements 1500 is shown schematically, wherein a first diffractive element receives light from a light source 1440. The further elements of the multiplicity of diffractive elements 1500 have a tree structure 1530.

In this case, the diffractive elements 1500 can be set up both to transmit light in the spectacle lens to the next diffractive element 1500 in the tree structure and to output couple light from the spectacle lens in order to steer light to an eye. As a result of the tree structure, the degree of freedom when designing a light distribution of the light that can be generated by the device 1100 is increased further.

Figure 13:
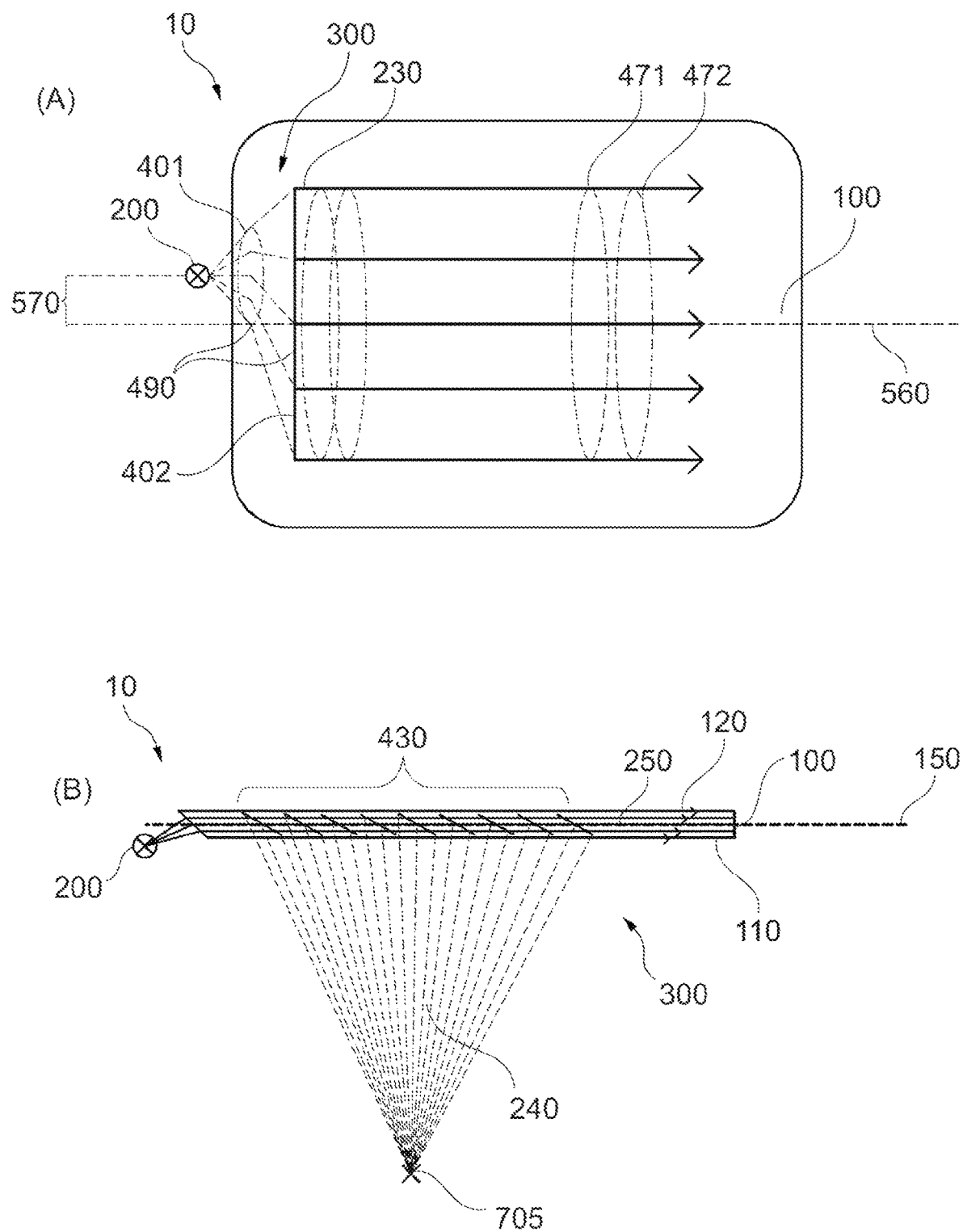

Further exemplary embodiments are shown in FIGS. 12, 13 and 14. Partial figures (A) each show a plan view of a spectacle lens 100. Partial figures (B) each show a lateral view. In the exemplary embodiments, light from a light source 200 is input coupled into the spectacle lens and steered to a focal point 705 by a group of diffractive elements 430, as described above.

In contrast to the exemplary embodiments in FIGS. 10 and 11, the light in the exemplary embodiments of FIGS. 12-14 is not subject to total-internal reflection but is guided as an expanded light beam 230 parallel to a spectacle lens plane 150. A beam expansion optical unit 490 comprising a first diffractive element 401 and a second diffractive element 402 is used to this end. The group of diffractive elements 430 is configured to receive the divergent light beam 220 from the first diffractive element 401 and provide said light beam as an expanded light beam 230.

In contrast to the exemplary embodiments in FIGS. 10 and 11, the light in the exemplary embodiment of FIGS. 12 to 14 is not subject to total-internal reflection but is guided as an expanded light beam 230 parallel to a spectacle lens plane 150. A beam expansion optical unit 490 comprising a first diffractive element 401 and a second diffractive element 402 is used to this end.

With a functional principle similar to that of a Galilean telescope, the beam expansion optical unit 490 can serve for expansion and subsequent collimation into the interior of the spectacle lens. The group of diffractive elements 430 can comprise a plurality of diffractive output coupling elements 470, for example first and second diffractive output coupling elements 471, 472.

The group of diffractive elements 430 can likewise be embodied as transmissive volume holograms, as shown in FIGS. 12 and 13, or as a reflective volume hologram, as shown in FIG. 14, or as a combination thereof. The devices and optical arrangements 300 described in the context of FIGS. 1B, 2 and 4 to 6 can also be used for the expansion optical unit.

In some examples, the diffractive elements require an angle deflection for beam shaping. By way of example, this may be the case if volume holograms are used as diffractive elements 401, 402. In these cases, an arrangement of first and second diffractive element 401, 402 as shown in FIG. 12 may be suboptimal since the center ray 560 of the beam does not experience a deflection. This can be improved by a lateral offset of the light source 200 with respect to the desired center ray 560 of the beam, as shown in FIGS. 13 and 14.

The offset 570 can be chosen to be even greater (not shown) such that it is not only the center ray 560 that is deflected but all of the light of the expanded light beam 230 by virtue of the offset 570 being increased until the light source is arranged for example above the region of the expanded light beam 230 in the plan view (A) of FIGS. 12 to 14.

Figure 16:
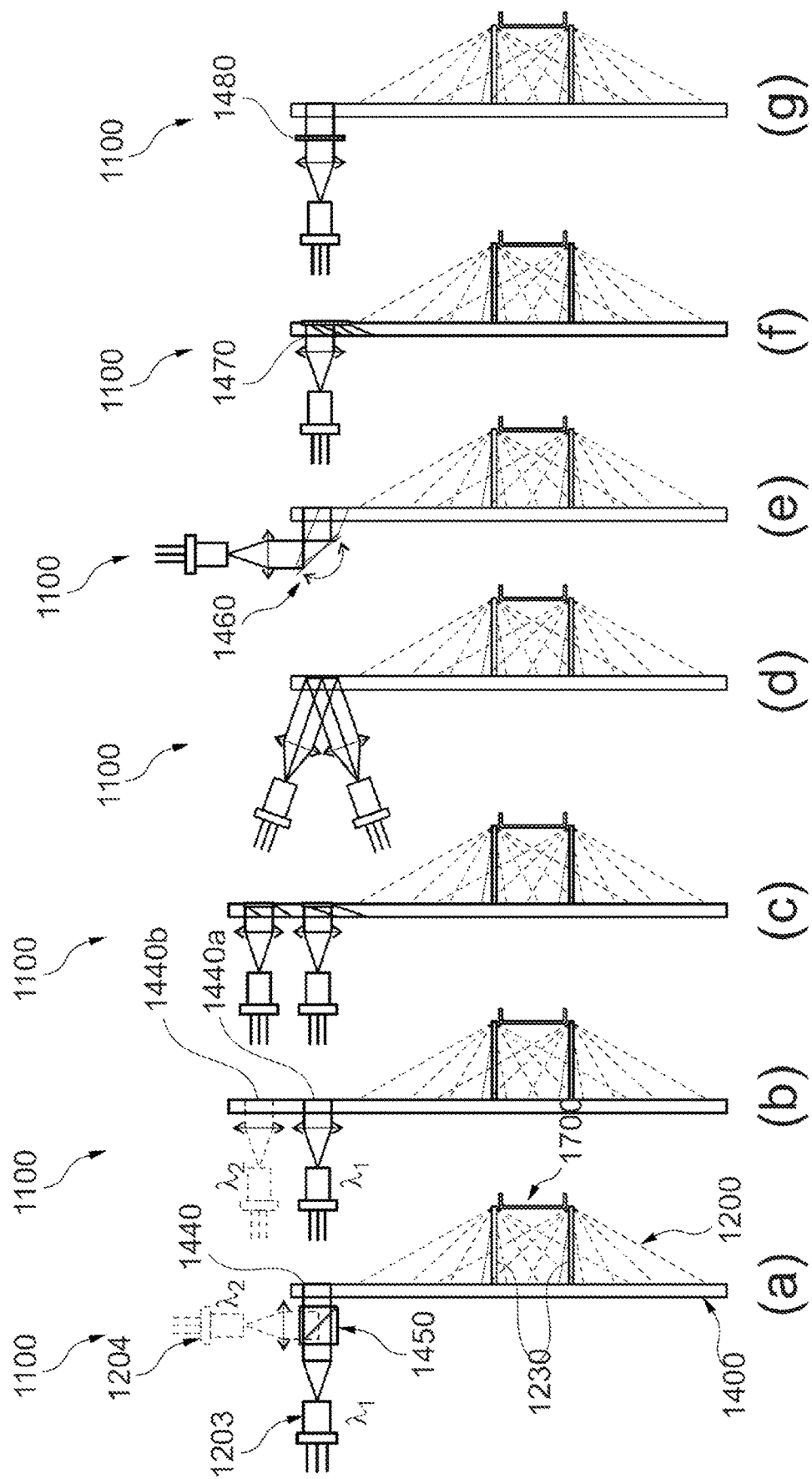
FIG. 16 shows devices according to various exemplary embodiments, which are multi-channel and/or switchable.

FIG. 16 shows devices according to various exemplary embodiments, which are multi-channel and/or switchable. In this case, light from two different light sources, for example, can be used. By way of example, light from one light source can serve to supply power to an ocular implant as described above while light from another light source serves other purposes, for example for illumination or for the projection of information. In other exemplary embodiments different wavelengths can be provided to supply ocular implants. In yet other exemplary embodiments, light with different light distributions can be provided to supply ocular implants. By way of example, a line of sight of the eye can be captured by means of an eye tracker and a light distribution can be selected on the basis of the line of sight in order to efficiently supply power to the ocular implant for the respective line of sight. In this way, the ocular implant can also be supplied over a large field of view. By way of example, a line of sight of the eye can be monitored by a so-called eye tracker and the light distribution can be chosen on the basis of the line of sight in order to optimize a power supply for the implant and/or in order to ensure that the greatest possible portion of the emitted energy reaches the ocular implant.

In this case, the partial figures of FIG. 16(*a*) to FIG. 16(*g*) show different examples of multi-channel or switchable devices which are configured to provide different light distributions, for example for supplying power to an ocular implant.

Different concepts of multi-channel optical waveguide systems are described below on the basis of devices 1100 in (a) to (g). The concepts can make use of high spectral and/or angular selectivity of diffractive elements as already explained in the aforementioned exemplary embodiments, for example volume holograms or other microstructured optical elements, in order to be able to transmit a plurality of beams independently of one another within the same volume of a spectacle lens that serves as a light guide 1400. In this context, a high spectral selectivity is understood to mean the drop in efficiency of the element by for example 50% of the full width at half maximum (FWHM) in the case of wavelength deviations from the design wavelength of for example <40 nm, for example <10 nm.

A high angular selectivity is understood to mean a drop in the efficiency of the element by 50% of the FWHM in the case of a deviation of the ray angle of incidence from a design angle for which the respective optical element is designed, for example in order to receive an associated input light beam from this angle, of for example <10°, for example <2°. In such cases, without being restricted thereto, a plurality of beams can propagate in different directions and/or with different wavelengths within the same volume of the optical waveguide 1400 and can be selectively coupled and transmitted by associated optical elements, which are sometimes also described as "fitting". Expressed differently, selectively acting replication regions that may be provided by buried diffractive elements can be provided within an identical volume of the light guide 1400. Replication regions are configured to receive at least one associated input light beam with an input beam profile and to provide a multiplicity of associated output light beams with respective output beam profiles, for example output couple one light beam from a spectacle lens and transmit another light beam in the spectacle lens. These replication regions can operate in superposition and convert the light for different characteristics, for example angles of incidence, into different light distributions. Sometimes this is also described as multiplexing, for example spectral multiplexing, if the optical elements, for example volume holograms, are set up such that they have a different coupling behavior for different spectral properties of the light.

Other types of multiplexing are also possible, for example angle- or polarization-dependent multiplexing, and combinations thereof.

This basic idea is briefly explained below using the example of side views of the device 1100 in FIG. 16. In this case, only a maximum of two light sources are shown in exemplary fashion even though this naturally should not be construed as restrictive; more complex systems with for example more than two light sources are also possible.

The device at (a) shows an device 1100 which is configured to receive light from a first light source 1203 at a first wavelength λ1 and light at a second wavelength λ2 from a second light source 1204, and to generate a light distribution 1200 for each wavelength received. In the example shown, the light distribution 1200 comprises a light distribution which is composed from the light distribution 1200, for example for supplying power to an ocular implant, and a light distribution of fixation markers 1230. Such a structure may be advantageous in that it is possible to provide various light distributions in different wavelength ranges for different purposes using the same optical waveguide 1400, for example the fixation markers 1230 at a wavelength λ2 of the second light source 1204 in the visible range and infrared light at a wavelength λ1 of the first light source 1203 in the infrared in the example shown. It is also possible for both light sources to transmit in the infrared at different wavelengths, in particular for generating different light distributions for supplying power to the ocular implant.

FIG. 16(b) shows an alternative implementation of the device of FIG. 16(a) with a differently designed input coupling element 1440. Input coupling elements described with reference to FIG. 16 can be realized with diffractive elements, in particular buried diffractive elements. In this exemplary embodiment, the input coupling element 1440 comprises two different regions, a first input coupling region 1440A being configured to input couple the light from the first light source 1203 and a second input coupling region 1440B being configured to input couple the light from the second light source 1204 into the optical waveguide 1400.

FIG. 16(c) to FIG. 16(g) show different options for realizing switchable systems and/or systems that facilitate a plurality of light distributions in overlaid fashion, which is sometimes also referred to as a superposition.

In the example of FIG. 16(c), the light sources 1203, 1204 are arranged with lateral offset and are input coupled by input coupling elements 1440A, 1440B into the optical waveguide 4100 at different points.

In this case, the respective associated input coupling elements 1440A, 1440B can be configured in such a way that different types of input coupling into the optical waveguide 1400 are achieved, for example different input coupling angles, even in the case of light sources 1203, 1204 of the same kind. Consequently, the device 1100 can be configured to provide two light distributions, a respective light distribution per light source in the example shown. In some examples, these light distributions can be chosen independently of one another, for example on account of the above-described angle selectivity and/or wavelength selectivity of the utilized optical elements.

FIG. 16(d) shows a variation of FIG. 16(c), wherein the two light sources 1204, 1203 are incident on an input coupling element 1440 at different angles. The latter is configured to input couple the two light sources into the optical waveguide 1400 independently of one another. Only one light source 1203 is present in the example of FIG. 16(e). In this case, the angle of incidence of the light of the light source 1203 is varied by a scanning mirror 1460, as a result of which a switchable light distribution arises. A switchable optical element 1470, for example a switchable hologram, is present in the optical waveguide 1400 in the example of FIG. 16(f). This can also achieve a superposition of different light distributions. In the example of FIG. 16(g), a polarization-changing element 1480 changes the polarization properties of the light from the light source 1203. The optical elements of the device 1100 may have polarization-dependent properties such that different light distributions can also be brought about by varying the polarization of the light incident on the device 1100.

The examples shown in FIG. 16(a) to FIG. 16(g) can also be combined with one another. By way of example, different light sources with different polarization directions—corresponding to the example of FIG. 16(g)—can be combined with a scanning mirror—as shown in FIG. 16(e). However, any other combination of the shown elements and procedures is also possible.

An opening in the spectacle lens may be desirable in some exemplary embodiments, for example in order to be able to carry out examinations of the eye using an examination modality. In order to nevertheless provide a suitable light distribution of light for supplying power to an ocular implant, such an device can be configured in that case as explained with reference to FIGS. 17A, 17B and 18.

Figure 17B:
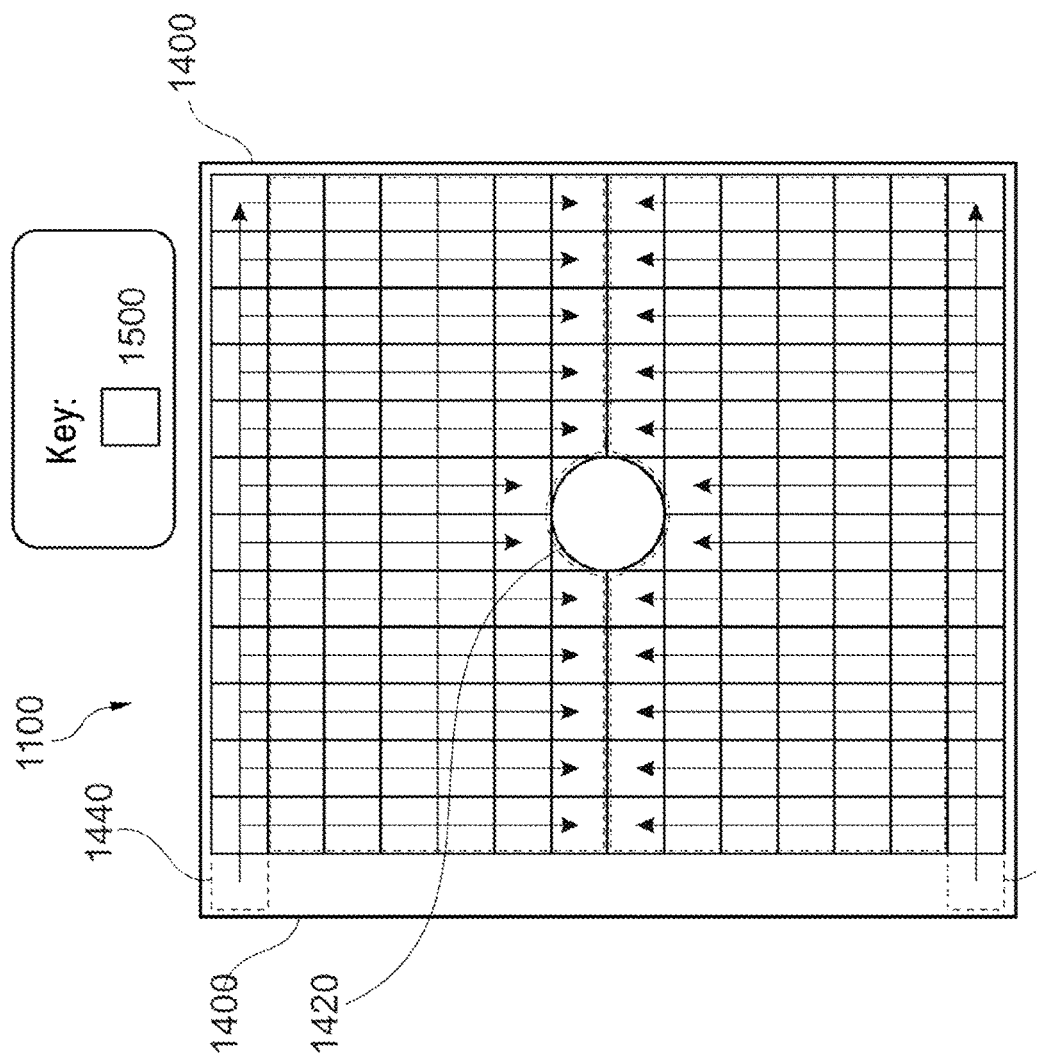
FIG. 17B shows a frontal view of the device of FIG. 17A.
Figure 17A:
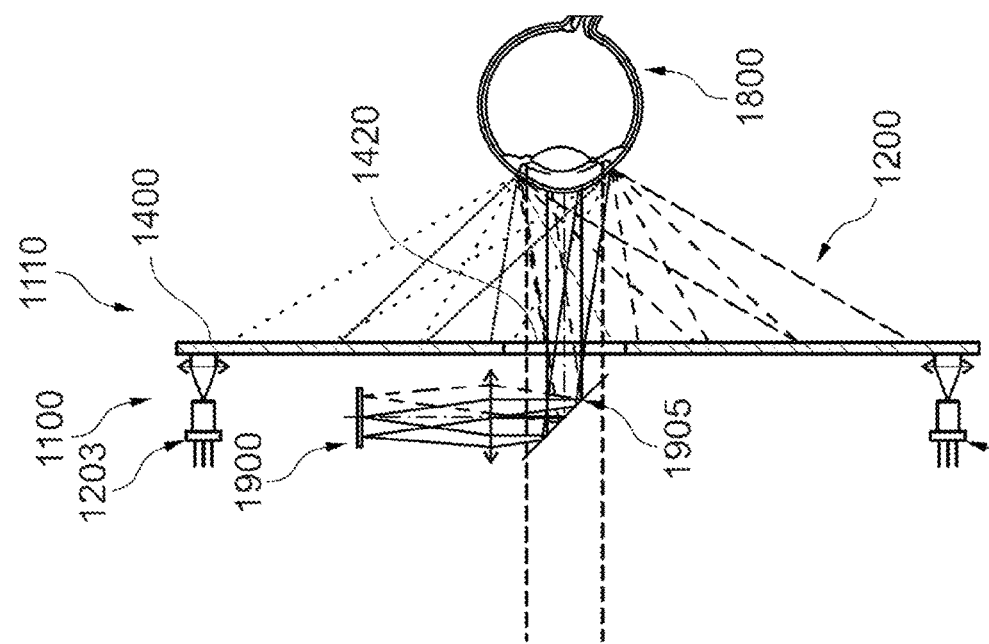
FIG. 17A shows a side view of a device which facilitates an examination modality.

FIG. 17A shows a lateral view of an device 1100 according to an exemplary embodiment. FIG. 17B shows a frontal view of the device 1100.

A light distribution 1200 for supplying power to an ocular implant of an eye 1800 is provided by the device 1100, wherein use is made of buried diffractive elements, as described above. Using a switchable device as explained with reference to FIG. 16, it is possible in some exemplary embodiments, in switchable fashion, to provide a light distribution for illuminating the eye for an examination, for example for keratometric measurement of the cornea of the eye 1800. Moreover, the eye can be examined through a cutout 1420 in a spectacle lens that serves as an optical waveguide 1400. By way of example, in the case of the aforementioned keratometric examination, the light reflected by the cornea of the eye 1800 can be detected by a detection device 1900 along a detection beam path 1905 and said light can subsequently be analyzed in order to deduce the topology of the cornea. As mentioned, the optical waveguide 1400 of the device 1100 has the cutout 1420. In order to obtain a light distribution 1200 suitable for supplying power to an ocular implant or else for illuminating purposes, for example for keratometry, in spite of the cutout 1420, said light distribution covering an entire visual field of the eye 1800 where possible or illuminating the entire eye to be examined, the light is provided by two light sources 1203, 1204 and input coupled by two input coupling elements 1440, 1441, which each may comprise buried diffractive elements. Proceeding from the respective input coupling elements 1440, 1441, the light is replicated by way of a multiplicity of replication regions and output coupled as light distribution 1200 in the direction of the eye 1800.

In the example of the device shown, the surface normal of the optical waveguide 1400 is arranged in parallel with a principal visual axis of the eye 1800. However, in other exemplary embodiments, the normal of the optical waveguide can be arranged precisely not in parallel with the principal visual axis of the eye 1800. By way of example, this can reduce or avoid reflections.

Figure 18:
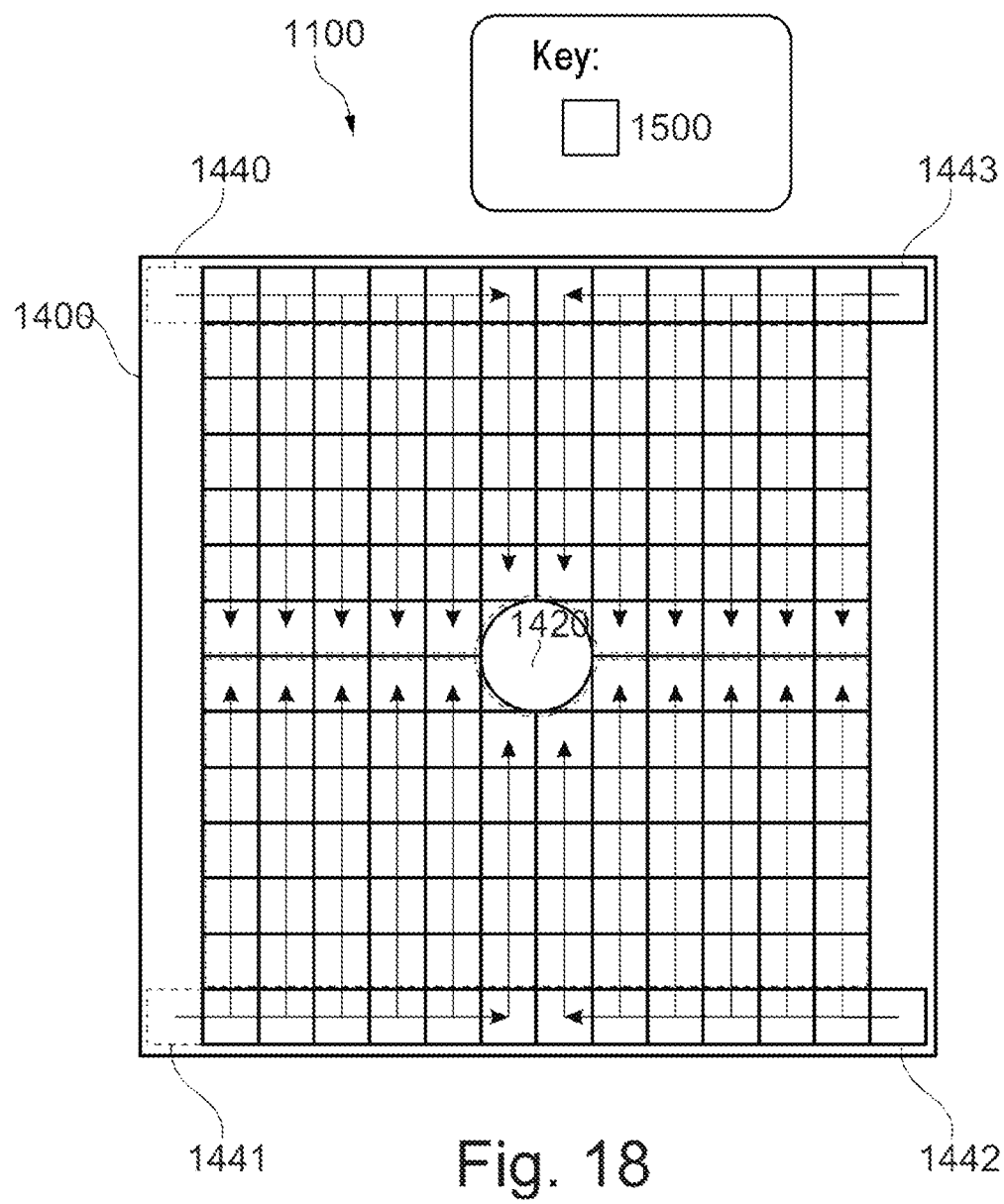
FIG. 18 shows a further exemplary embodiment of a device which facilitates an examination modality.

FIG. 18 shows a further exemplary embodiment of an device 1100 as a development of the device in FIGS. 17A, 17B.

Four input coupling elements 1440 to 1443 are present in the device 1100 of FIG. 18 and these can in turn be realized with buried diffractive elements as explained above. The multiplicity of replication regions 1500 are coupled in such a way with one another here that a light distribution such as the light distribution 1200 in FIG. 7A can be provided by the multiplicity of replication regions 1500.

An improved device for supplying power to active ocular implants can be provided by the exemplary embodiments shown here.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products. Moreover, features or aspects of various example embodiments may be mixed and matched (even if such combination is not explicitly described herein) without departing from the scope of the invention.

The invention claimed is:

1. A device for supplying power to an active ocular implant in an eye of a user, comprising:
 a spectacle lens with a first main surface and a second main surface;
 a light source; and
 an optical arrangement which is configured to input couple light from the light source into the spectacle lens and output couple the light from the first main surface of the spectacle lens to the user,
 wherein the optical arrangement comprises at least one diffractive element which is arranged in the spectacle lens,
 wherein each of the at least one diffractive element includes an associated first end and an associated second end, and
 wherein the associated first end and the associated second end each have a different distance from the first main surface and/or each have a different distance from the second main surface, and
 wherein the at least one diffractive element comprises a first diffractive element which is configured to receive a collimated light beam and provide the collimated light beam as a divergent light beam.

2. The device of claim 1, wherein the at least one diffractive element comprises a second diffractive element which is configured to receive the divergent light beam from the first diffractive element and provide the divergent light beam as an expanded light beam.

3. The device of claim 2, wherein the expanded light beam extends in at least one reception direction.

4. The device of claim 1, wherein the at least one diffractive element comprises a group of diffractive elements, each of which is configured to receive light from a respective reception direction and to deflect a first portion of the light in a respective deflection direction and to transmit a second portion of the light in a respective transmission direction, wherein a first group element of the group of diffractive elements is configured to receive light from the light source.

5. The device of claim 4, wherein the group of diffractive elements comprises a second group element which is arranged such that it transmits light in its transmission direction to a third group element in a reception direction of the third group element.

6. The device of claim 5, wherein the group of diffractive elements is configured such that a respective ratio of the first portion to the second portion increases with the number of group elements of the group of diffractive elements that have been traversed by the light in the spectacle lens.

7. The device of claim 4, wherein the device is configured to output couple the light into the respective deflection direction toward the user.

8. A device for supplying power to an active ocular implant in an eye of a user, comprising:
 a spectacle lens with a first main surface and a second main surface;
 a light source; and
 an optical arrangement which is configured to input couple light from the light source into the spectacle lens and output couple the light from the first main surface of the spectacle lens to the user,
 wherein the optical arrangement comprises at least one diffractive element which is arranged in the spectacle lens,
 wherein each of the at least one diffractive element includes an associated first end and an associated second end, and
 wherein the associated first end and the associated second end each have a different distance from the first main surface and/or each have a different distance from the second main surface, and
 wherein the optical arrangement comprises at least one diffractive output coupling element which is configured to receive light from the at least one diffractive element and to output couple the light to the user.

9. The device of claim 8, wherein the at least one diffractive output coupling element is configured to output couple the light to the user with effective focusing.

10. A device for supplying power to an active ocular implant in an eye of a user, comprising:
   a spectacle lens that has a first main surface and a second main surface;
   a light source; and
   an optical arrangement which is configured to input couple light from the light source into the spectacle lens and output couple said light from the first main surface of the spectacle lens to the user,
   wherein the optical arrangement comprises at least one diffractive deflection element which is configured to receive a light beam from a first direction and transmit the light beam in a second direction from a number of possible directions,
   wherein the second direction depends on:
      an angle of incidence between the light beam and the at least one diffractive deflection element, and/or
      a wavelength of the light beam, and/or
      a switching state of the at least one diffractive deflection element,
   wherein at least one of the diffractive deflection elements is a volume hologram,
   wherein the at least one diffractive element comprises at least two diffractive elements,
   wherein the at least two diffractive elements each comprise a volume hologram, and
   wherein one of the at least two diffractive elements comprises a transmissive volume hologram and the other of the at least two diffractive elements comprises a reflective volume hologram.

11. The device of claim 10, wherein the at least one diffractive deflection element comprises a multiply exposed volume hologram, wherein the number of possible directions is based on a number of multiple exposures of the multiply exposed volume hologram.

12. The device of claim 10, wherein the at least one diffractive deflection element comprises a first diffractive deflection element and a second diffractive deflection element, wherein the first and the second diffractive deflection elements are arranged at least partly separately in the spectacle lens and are each configured to transmit light to at least one diffractive output coupling element.

13. The device of claim 10, wherein the at least one diffractive deflection element comprises at least one volume hologram arranged in the spectacle lens.

14. The device of claim 10, wherein a first deflection element of the at least one diffractive deflection element is configured to convert the light beam into a divergent deflected light beam such that the optical arrangement is configured to emit the divergent deflected light beam in the second direction.

15. The device of claim 10, wherein at least one diffractive element is arranged in at least one of the number of possible directions and/or wherein the at least one diffractive deflection element comprises the at least one diffractive element.

16. The device of claim 10, wherein the first main surface and/or the second main surface has at least one curve.

17. The device of claim 10, wherein the spectacle lens has a cutout.

18. A device for supplying power to an active ocular implant in an eye of a user, comprising:
   a spectacle lens that has a first main surface and a second main surface;
   a light source; and
   an optical arrangement which is configured to input couple light from the light source into the spectacle lens and output couple said light from the first main surface of the spectacle lens to the user,
   wherein the optical arrangement comprises at least one diffractive deflection element which is configured to receive a light beam from a first direction and transmit the light beam in a second direction from a number of possible directions,
   wherein the second direction depends on:
      an angle of incidence between the light beam and the at least one diffractive deflection element, and/or
      a wavelength of the light beam, and/or
      a switching state of the at least one diffractive deflection element,
   wherein the optical arrangement comprises at least one diffractive output coupling element which is configured to receive light from the at least one diffractive element and to output couple the light to the user, and
   wherein the at least one diffractive output coupling element comprises a first output coupling element and a second output coupling element, and wherein the number of possible directions comprises a direction from the at least one diffractive deflection element to the first output coupling element and a direction from the at least one diffractive deflection element to the second output coupling element.

19. A device for supplying power to an active ocular implant in an eye of a user, comprising:
   a spectacle lens that has a first main surface and a second main surface;
   a light source; and
   an optical arrangement which is configured to input couple light from the light source into the spectacle lens and output couple said light from the first main surface of the spectacle lens to the user,
   wherein the optical arrangement comprises at least one diffractive deflection element which is configured to receive a light beam from a first direction and transmit the light beam in a second direction from a number of possible directions,
   wherein the second direction depends on:
      an angle of incidence between the light beam and the at least one diffractive deflection element, and/or
      a wavelength of the light beam, and/or
      a switching state of the at least one diffractive deflection element, and
   wherein the light source comprises at least one of the following elements:
   two individual light sources which are configured to provide light in different directions and/or in different wavelength ranges and/or at different illumination positions of at least one input coupling element of the optical arrangement,
   a beam splitter,
   a scanning mirror, and
   a switchable element.

20. The device of claim 19, wherein the device is configured to switch between at least two different light distributions of the light depending on a line of sight of the eye.

* * * * *